(12) United States Patent
Hara et al.

(10) Patent No.: US 11,694,791 B2
(45) Date of Patent: Jul. 4, 2023

(54) ON-BOARD APPARATUS, FIRST INFORMATION PROCESSING APPARATUS, INFORMATION PROCESSING SYSTEM, AND INFORMATION PROCESSING METHOD

(71) Applicant: TOYOTA JIDOSHA KABUSHIKI KAISHA, Toyota (JP)

(72) Inventors: Yusuke Hara, Musashino (JP); Shuhei Aketa, Koto (JP); Toru Yanagida, Nagoya (JP); Shin Sakurada, Toyota (JP); Tae Sugimura, Miyoshi (JP); Yasutaka Ujihara, Meguro (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 303 days.

(21) Appl. No.: 16/992,533

(22) Filed: Aug. 13, 2020

(65) Prior Publication Data
US 2021/0048301 A1 Feb. 18, 2021

(30) Foreign Application Priority Data
Aug. 13, 2019 (JP) .................................. 2019-148600

(51) Int. Cl.
G16H 40/20 (2018.01)
G01C 21/34 (2006.01)
G01C 21/36 (2006.01)

(52) U.S. Cl.
CPC .......... *G16H 40/20* (2018.01); *G01C 21/343* (2013.01); *G01C 21/3602* (2013.01)

(58) Field of Classification Search
None
See application file for complete search history.

(56) References Cited

U.S. PATENT DOCUMENTS

| | | | |
|---|---|---|---|
| 2014/0200913 A1* | 7/2014 | Budhrani | G16H 10/60 705/2 |
| 2016/0143626 A1 | 5/2016 | Ohta et al. | |
| 2016/0188829 A1* | 6/2016 | Southerland | H04N 7/15 705/2 |
| 2017/0018007 A1* | 1/2017 | DeFrank | G16H 50/20 |
| 2017/0154160 A1* | 6/2017 | Walker | G16H 40/67 |

(Continued)

FOREIGN PATENT DOCUMENTS

| | | |
|---|---|---|
| JP | 2013119014 A | 6/2013 |
| JP | 2015029620 A | 2/2015 |

(Continued)

*Primary Examiner* — Anne Marie Antonucci
*Assistant Examiner* — Amelia Vorce
(74) *Attorney, Agent, or Firm* — Oliff PLC

(57) ABSTRACT

A medical treatment server is configured to reduce load on physicians for work other than examination and treatment. The server is configured to send recruiting conditions and in response receive undertaking conditions that are related to a physician who does not belong to the medical facility. A controller decides whether to appoint the physician depending on whether a pickup location included in the received undertaking conditions is apart from a location of the medical facility by a distance equal to or greater than a threshold. Upon deciding to appoint the physician, the controller determines a pickup location included in the undertaking conditions to be a stopover point.

10 Claims, 14 Drawing Sheets

(56) References Cited

U.S. PATENT DOCUMENTS

| | | | |
|---|---|---|---|
| 2017/0193182 A1* | 7/2017 | Mihai | G16H 80/00 |
| 2017/0300654 A1* | 10/2017 | Stein | H01Q 1/42 |
| 2017/0345114 A1* | 11/2017 | Brandt | G06Q 10/02 |
| 2018/0218338 A1* | 8/2018 | Hengerer | G06F 16/24575 |
| 2019/0066505 A1* | 2/2019 | Salvucci | G08G 1/144 |
| 2019/0189277 A1 | 6/2019 | Toyoda et al. | |
| 2019/0385753 A1* | 12/2019 | Aganyan | G16H 15/00 |
| 2020/0117195 A1 | 4/2020 | Yasui et al. | |
| 2020/0143940 A1* | 5/2020 | Yasui | G06Q 50/22 |
| 2020/0228631 A1* | 7/2020 | Ward | H04L 67/12 |
| 2021/0020305 A1* | 1/2021 | Ray | G16H 80/00 |
| 2022/0130531 A1* | 4/2022 | Kadri | G16H 80/00 |

FOREIGN PATENT DOCUMENTS

| | | |
|---|---|---|
| JP | 2018-139156 A | 9/2018 |
| JP | 2019109763 A | 7/2019 |
| WO | 2018230559 A1 | 12/2018 |

\* cited by examiner

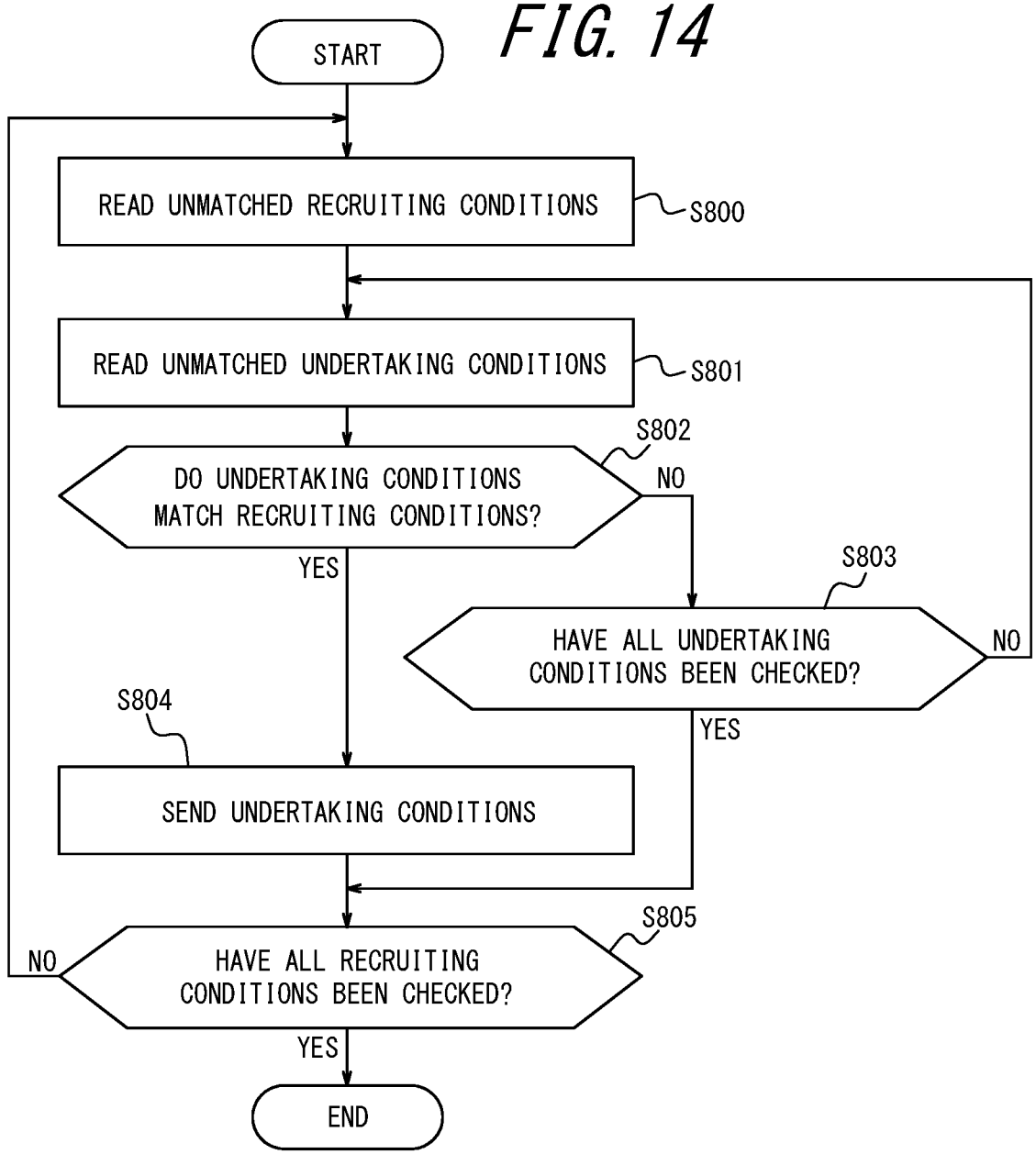

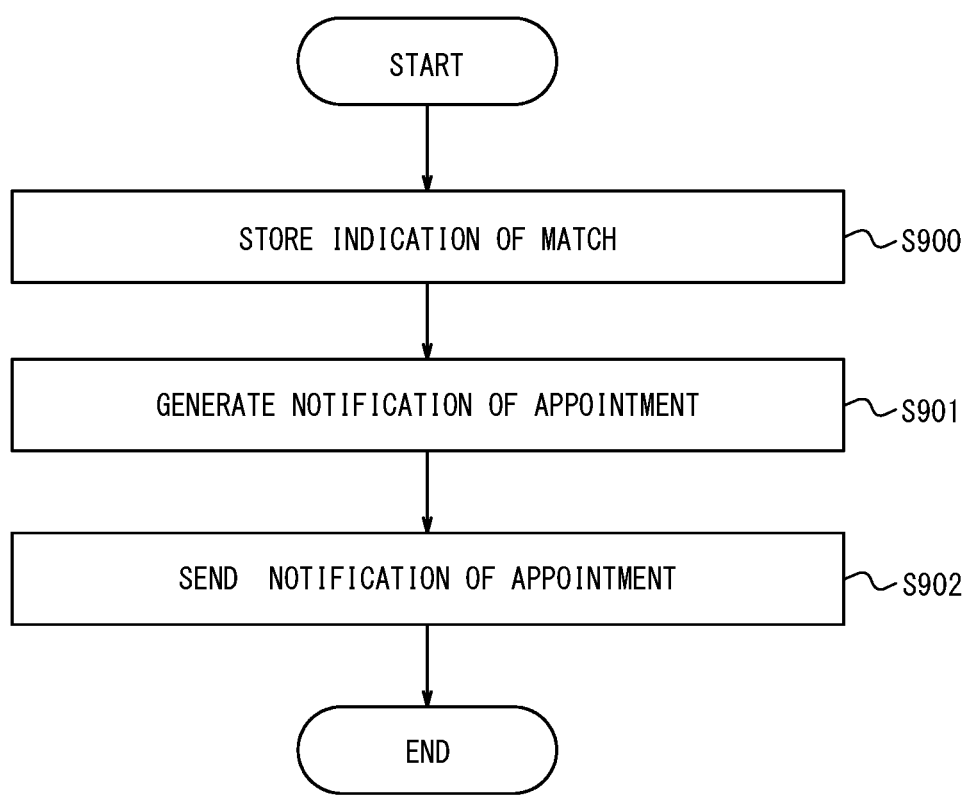

ON-BOARD APPARATUS, FIRST INFORMATION PROCESSING APPARATUS, INFORMATION PROCESSING SYSTEM, AND INFORMATION PROCESSING METHOD

CROSS-REFERENCE TO RELATED APPLICATION

The present application claims priority to Japanese Patent Application No. 2019148600 filed on Aug. 13, 2019, the entire disclosure of which is incorporated herein by reference.

TECHNICAL FIELD

The present disclosure relates to an on-board apparatus, a first information processing apparatus, an information processing system, and an information processing method.

BACKGROUND

Various technologies have been developed for reducing load on physicians for work other than examination and treatment. For example, PTL 1 discloses an information processing apparatus for reducing duplicate data input operations on electronic health records and order entry systems for ordering tests (refer to PTL 1).

CITATION LIST

Patent Literature

PTL 1: JP2018139156A

SUMMARY

The information processing apparatus described in PTL 1 can reduce load on physicians for work other than examination and treatment, and as a result, time can be used to provide more patients with medical services. However, there have also been demands for other technologies for reducing load on physicians for work other than examination and treatment.

An object of the present disclosure having been made in consideration of the circumstances described above is to reduce load on physicians for work other than examination and treatment.

An on-board apparatus according to an embodiment of the present disclosure includes an input interface configured to detect a user input for designating a relative position on a living body targeted for medical examination, a communication interface configured to send the relative position to a first information processing apparatus and receives from the first information processing apparatus a first sound detected at the relative position and/or a first subject image detected at the relative position, and an output interface configured to output the first sound and/or the first subject image.

A first information processing apparatus according to an embodiment of the present disclosure includes a communication interface configured to receive a relative position on a living body targeted for medical examination from an on-board apparatus and a sensor configured to detect a first sound of the living body and/or a first subject image of the living body. The communication interface sends the first sound detected at the relative position and/or the first subject image detected at the relative position, to the on-board apparatus.

An information processing system according to an embodiment of the present disclosure includes a first information processing apparatus and an on-board apparatus. The first information processing apparatus includes a communication interface configured to receive a relative position on a living body targeted for medical examination from the on-board apparatus and a sensor configured to detect a first sound of the living body and/or a first subject image of the living body. The communication interface sends the first sound detected at the relative position and/or the first subject image detected at the relative position, to the on-board apparatus. The on-board apparatus includes an input interface configured to detect a user input for designating the relative position, a communication interface configured to send the relative position to the first information processing apparatus and receives, from the first information processing apparatus, the first sound detected at the relative position and/or the first subject image detected at the relative position, and an output interface configured to output the first sound and/or the first subject image.

An information processing method according to an embodiment of the present disclosure is implemented by a first information processing apparatus. The first information processing apparatus includes a communication interface configured to receive a relative position on a living body targeted for medical examination from the on-board apparatus and a sensor configured to detect a first sound of the living body and/or a first subject image of the living body. The communication interface sends the first sound detected at the relative position and/or the first subject image detected at the relative position, to the on-board apparatus. The communication interface sends a designated time, a stopover point, and a destination to the on-board apparatus. The first information processing apparatus includes sending recruiting conditions including a clinical department and a medical service request time, to a second information processing apparatus and, when, in response to the sent recruiting conditions, receiving undertaking conditions matching the recruiting conditions from the second information processing apparatus, sending a decision on appointment with respect to the undertaking conditions, to the second information processing apparatus.

The on-board apparatus, the first information processing apparatus, the information processing system, and the information processing method according to an embodiment of the present disclosure can reduce load on physicians for work other than examination and treatment.

BRIEF DESCRIPTION OF THE DRAWINGS

In the accompanying drawings:

FIG. 14 is a flowchart illustrating matching processing performed by a controller in FIG. 6; and FIG. 15 is a flowchart illustrating appointment notification processing performed by the controller in FIG. 6.

DETAILED DESCRIPTION

Hereinafter, an embodiment of the present disclosure will be described with reference to the drawings.

Figure 1:
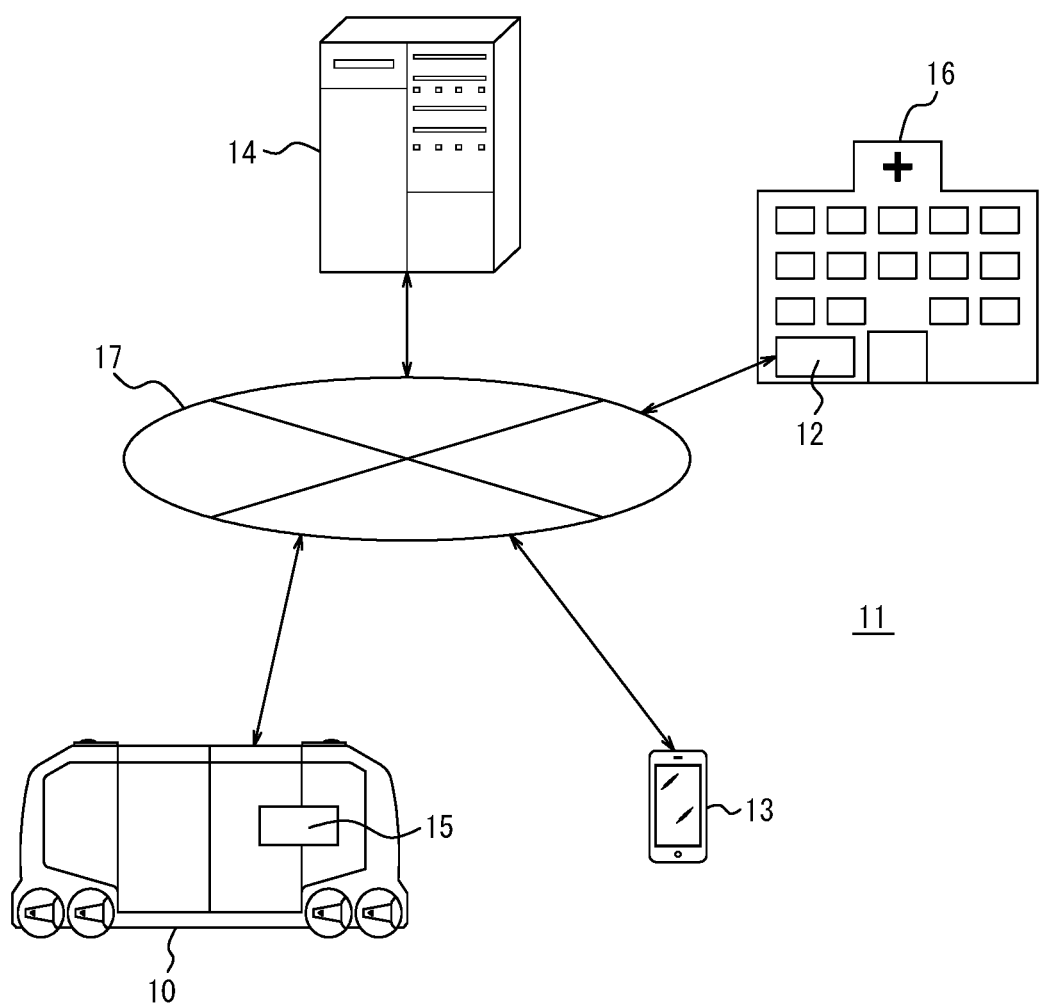
FIG. 1 is a configuration diagram illustrating an overall configuration of an information processing system including a vehicle according to an embodiment of the present disclosure.

An information processing system 11 including a vehicle 10 according to an embodiment of the present disclosure will be outlined with reference to FIG. 1. The information processing system 11 includes the vehicle 10, a first information processing apparatus 12, a first terminal apparatus (a terminal apparatus) 13, and a second information processing apparatus 14.

For example, the vehicle 10 is, but not limited to, an autonomous driving vehicle capable of performing autonomous driving or follow-up driving; the vehicle 10 may be any vehicle in which a second terminal apparatus (an on-board apparatus) 15 can be installed. The first information processing apparatus 12 includes one server apparatus or a plurality of server apparatuses capable of communicating with each other. The first information processing apparatus 12 is installed in a medical facility 16. The first terminal apparatus 13 is, for example, a general electronic device such as a smartphone or a personal computer (PC), but the first terminal apparatus 13 is not limited to this example and may be an electronic device especially for the information processing system 11. The first terminal apparatus 13 is owned by, for example, a physician. The second information processing apparatus 14 includes one server apparatus or a plurality of server apparatuses capable of communicating with each other. While FIG. 1 illustrates one vehicle 10, one first information processing apparatus 12, and one first terminal apparatus 13 for ease of description, the information processing system 11 only has to include at least one vehicle 10, at least one first information processing apparatus 12, and at least one first terminal apparatus 13.

The vehicle 10, the first information processing apparatus 12, the first terminal apparatus 13, and the second information processing apparatus 14 are each communicably connected to a network 17 involving, for example, a mobile communication network and the Internet. At least part of the information processing system 11 is used for providing a mobility service (Mobility-as-a-Service: MaaS). Service providers can provide mobility services such as a ridesharing service, a mobile hotel, and a mobile retail shop by using the second terminal apparatus 15 and the vehicle 10.

The outline of the present embodiment is further explained. The first information processing apparatus 12 installed in the medical facility 16 sends a designated time, a stopover point, and a final destination (a destination) to the vehicle 10. As used herein, the term "send" denotes sending information on a target such as a designated time. The vehicle 10 reaches a stopover point by a received designated time. As used herein, the term "receive" denotes receiving information on a target such as a designated time. A physician can be picked up by the vehicle 10 at a stopover point. After a physician is picked up by the vehicle 10, the vehicle 10 travels to a final destination such as the medical facility 16 or any parking space. While the vehicle 10 travels to the final destination, the physician in the vehicle 10 provides a medical service for a patient in a dedicated examination room of the medical facility 16 through communication between the vehicle 10 and the first information processing apparatus 12. The medical facility 16 has, for example, a physician belonging to the medical facility 16 provide a medical service through the communication described above. Alternatively, by using the second information processing apparatus 14, the medical facility 16 may seek a physician who undertakes the provision of medical service through the communication described above. The second information processing apparatus 14 determines whether a physician proposing undertaking conditions by using the first terminal apparatus 13 matches recruiting conditions of the medical facility 16. The second information processing apparatus 14 notifies the first information processing apparatus 12 of a physician proposing particular undertaking conditions that match recruiting conditions. As used herein, the term "notify" denotes providing information on a target such as a physician. When the first information processing apparatus 12 determines to appoint the physician of which information is provided, the vehicle 10 is moved to a pickup location designated by the physician.

Usually, physicians need to travel from their home to the medical facility 16 to provide medical services for patients at the medical facility 16. This means that travel for providing medical services puts strain on physicians. However, since the present embodiment described above enables a physician to provide a medical service during travel, it is possible to reduce time unused for medical services. As such, time unused for medical services are reduced and load on physicians for work other than examination and treatment is lightened.

Next, the constituents of the information processing system 11 are described in detail.

Figure 2:
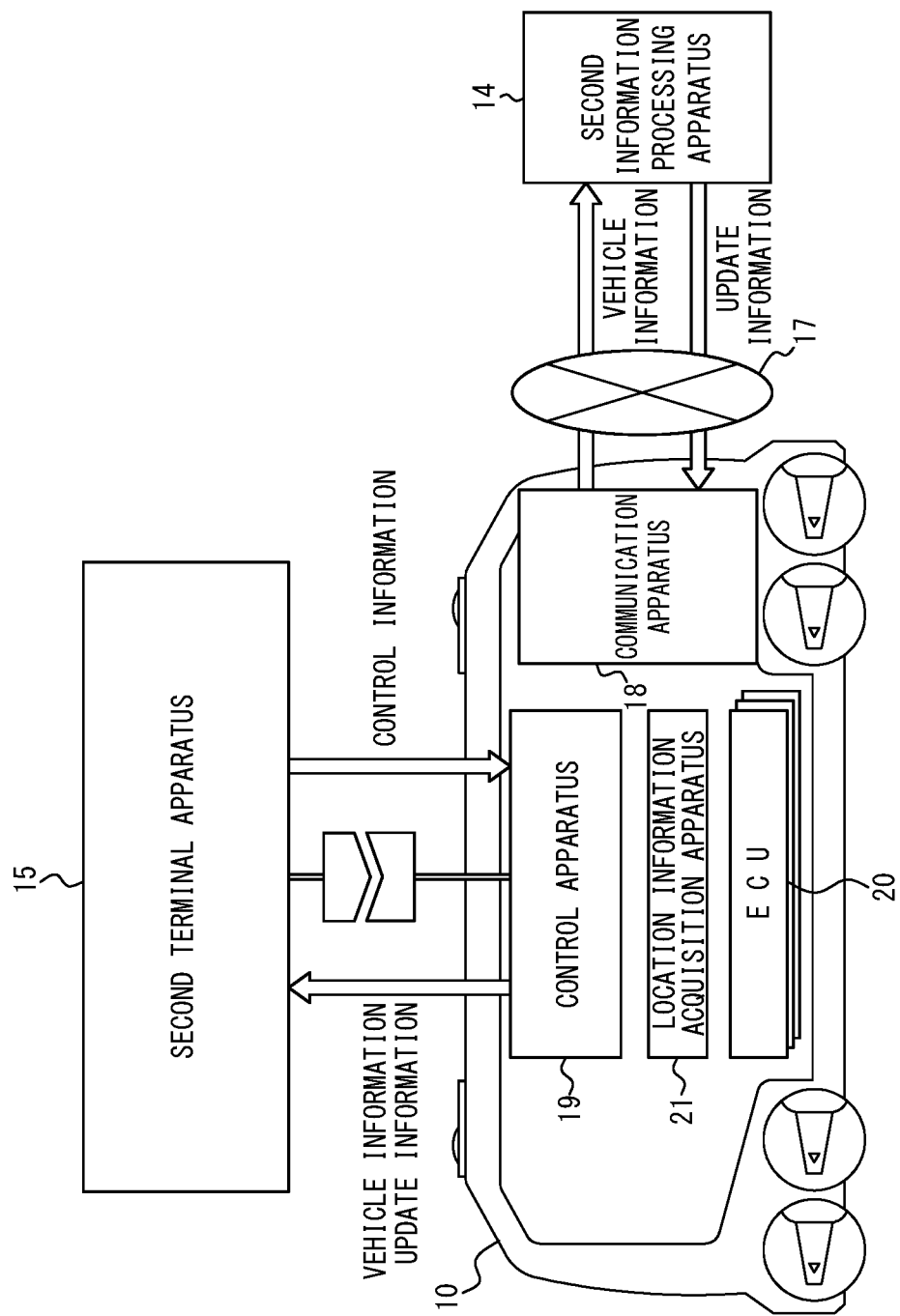
FIG. 2 is a functional block diagram schematically illustrating a configuration of the vehicle in FIG. 1.

As illustrated in FIG. 2, the vehicle 10 includes a communication apparatus 18, a control apparatus 19, a plurality of electronic control units (ECUs) 20, a location information acquisition apparatus 21, and the second terminal apparatus 15. The communication apparatus 18, the control apparatus 19, the plurality of ECUs 20, the location information acquisition apparatus 21, and the second terminal apparatus 15 are communicably connected to each other via, for example, an in-vehicle network such as a controller area network (CAN) or dedicated lines.

The vehicle 10 has at least one room in which a physician provides medical services. The room is separated from other space in the vehicle 10. Part of the second terminal apparatus 15 is provided individually for the room as described later. The vehicle 10 provides the room as a space in which a physician provides remote medical services by using the second terminal apparatus 15.

In the vehicle 10, the second terminal apparatus 15 automatically generates control information by using autonomous driving control software and sends the control information to the control apparatus 19. The control apparatus 19 performs vehicle control in accordance with the received control information and accordingly controls the vehicle 10 to drive. For example, the vehicle control is, but not limited to, autonomous driving control. At least part of an application programming interface (API) in which specifications of control information are defined is disclosed for service providers. Service providers can freely develop the autonomous driving control software of the second terminal apparatus 15 by programming with the use of the disclosed API. Thus, the service providers can provide any mobility service by installing a facility according to a purpose in a space of the vehicle cabin of the vehicle 10 and developing autonomous driving control software by programming with the use of an API according to the purpose.

The communication apparatus 18 includes a communication module configured to establish communication via an in-vehicle network or a dedicated line. The communication apparatus 18 also includes a communication module configured to establish connection with the network 17. For example, the communication apparatus 18 may include a communication module compliant with mobile communication standards such as the fourth generation (4G) and the fifth generation (5G). When the communication apparatus 18 sends information through the network 17, the communication apparatus 18 may add identification information on the vehicle 10 to the information. The identification information on the vehicle 10 is information that can be used for uniquely identifying the vehicle 10 in the information processing system 11.

The control apparatus 19 performs vehicle control in accordance with control information received from the second terminal apparatus 15. For example, the vehicle control is, but not limited to, autonomous driving control for reaching a final destination. The autonomous driving includes, for example, Levels 1 to 5 defined by the Society of Automotive Engineers (SAE), but the autonomous driving is not limited to this example and may be defined in any form. The vehicle control is performed by the control apparatus 19 and the ECUs 20 cooperating with each other. The control apparatus 19 includes a communication module configured to communicate with the second terminal apparatus 15, the communication apparatus 18, and the ECUs 20, one or more memories configured to store a system program, an application program, and the like, and a controller including one or more processors configured to control an operation of the entire control apparatus 19.

The control apparatus 19 receives, for example, various kinds of vehicle information (for example, a speed, a location, and a condition of autonomous driving) regarding the vehicle 10 from the ECUs 20 or the like. The control apparatus 19 sends the vehicle information to the second terminal apparatus 15 and also to the second information processing apparatus 14 by using the communication apparatus 18. The control apparatus 19 also receives update information for the system program and the like of the second terminal apparatus 15 from the second information processing apparatus 14 via the communication apparatus 18 and sends the update information to the second terminal apparatus 15. When control information is received from the second terminal apparatus 15, the control apparatus 19 performs vehicle control for the vehicle 10 in accordance with the control information.

The plurality of ECUs 20 control an operation of the vehicle 10 in cooperation with the control apparatus 19. Specifically, the plurality of ECUs 20 receive from the control apparatus 19 a control instruction based on control information and control the operation of the vehicle 10 in accordance with the control instruction. For example, the plurality of ECUs 20 control the operating variable of the vehicle 10 to reach a value indicated by a control instruction. The plurality of ECUs 20 collect measured values regarding the control or operating variable of the vehicle 10 from various sensors installed in the vehicle 10 at each control time and sends the measured values to the control apparatus 19.

The location information acquisition apparatus 21 includes at least one receiver for any satellite navigation system. For example, the location information acquisition apparatus 21 may include a global positioning system (GPS) receiver. The location information acquisition apparatus 21 obtains a measured value corresponding to a location of the vehicle 10 as location information and sends the measured value to the control apparatus 19.

Figure 3:
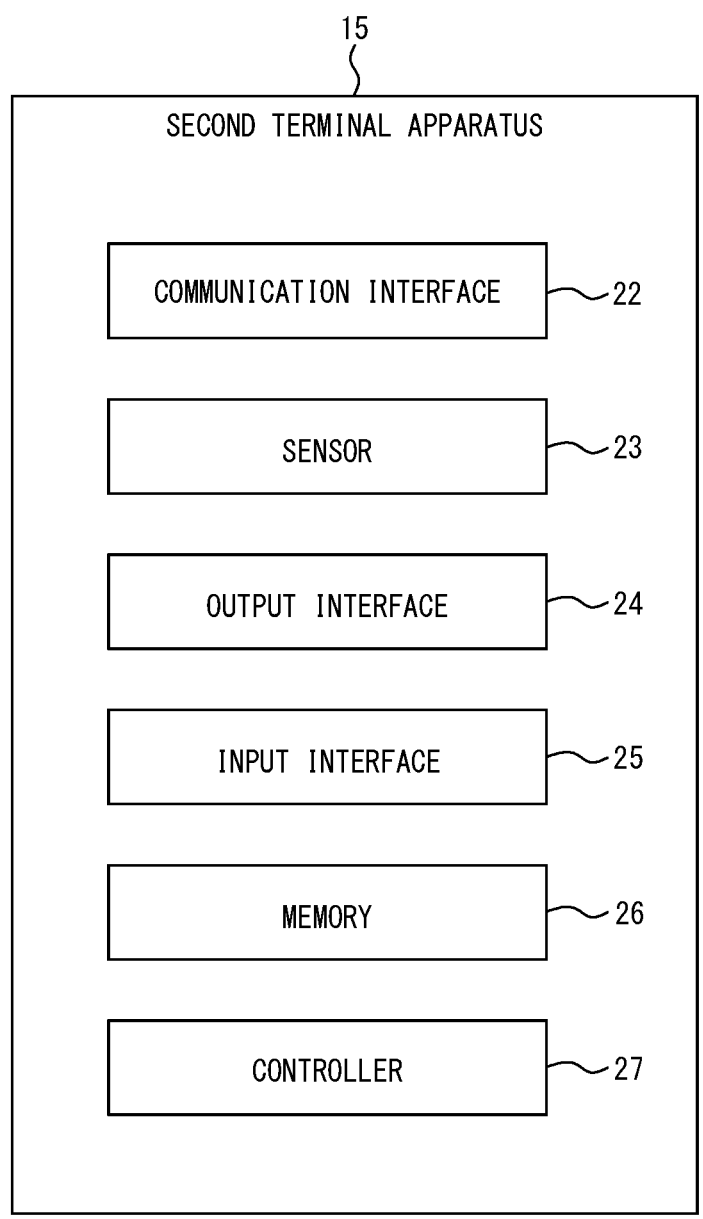
FIG. 3 is a functional block diagram schematically illustrating a configuration of a second terminal apparatus in FIG. 2.

As illustrated in FIG. 3, the second terminal apparatus 15 includes a communication interface 22, a sensor 23, an output interface 24, an input interface 25, a memory 26, and a controller 27. The second terminal apparatus 15 may include a plurality of the sensors 23. The plurality of the sensors 23 may be provided individually for rooms in the vehicle 10. The second terminal apparatus 15 may include a plurality of the output interfaces 24. The plurality of the output interfaces 24 may be provided individually for rooms in the vehicle 10. The second terminal apparatus 15 may include a plurality of the input interfaces 25. The plurality of the input interfaces 25 may be provided individually for rooms in the vehicle 10. Thus, in the case in which the vehicle 10 has a plurality of rooms, the sensor 23, the output interface 24, and the input interface 25 are provided for each of the plurality of rooms.

The communication interface 22 includes a communication module configured to communicate with the communication apparatus 18, the control apparatus 19, and the location information acquisition apparatus 21. In the present embodiment, the second terminal apparatus 15 is connected to the network 17 via the communication interface 22 and the communication apparatus 18. The communication interface 22 may include a communication module configured to establish connection with the network 17. For example, the communication interface 22 may include a communication module compliant with mobile communication standards such as 4G and 5G. For example, the communication interface 22 may include a communication module compliant with a short-distance wireless communication standard such as Bluetooth® (Bluetooth is a registered trademark in Japan, other countries, or both). The communication interface 22 sends and receives various kinds of information via at least the network 17. When the communication interface 22 directly sends information through the network 17, the communication interface 22 may add identification information on the second terminal apparatus 15 to the information. The identification information on the second terminal apparatus 15 is information that can be used for uniquely identifying the second terminal apparatus 15 in the information processing system 11.

The sensor 23 includes, for example, a sound collection sensor, such as a microphone, and detects a sound (hereinafter referred to as a "second sound") in the room. The sensor 23 may include an imaging sensor, such as a camera, and detect a subject image (hereinafter referred to as a "second subject image") in the room.

The output interface 24 includes at least one interface configured to output information to notify users. The output interface 24 includes, for example, a speaker configured to output information in the form of sound and outputs a first sound received by the communication interface 22 from the first information processing apparatus 12. Additionally, the output interface 24 includes, for example, a display configured to output information in the form of image and outputs a first subject image received by the communication interface 22 from the first information processing apparatus 12.

The input interface 25 includes at least one interface configured to detect user inputs. The input interface 25 includes, for example, a touch screen provided in combination with the display of the output interface 24. The touch screen detects a user input for designating a relative position on a living body targeted for examination such as a schematic human body displayed on a display as a position at which the first sound, the first subject image, or both are detected in the medical facility 16 equipped with the first information processing apparatus 12 as described later.

The memory 26 is, but not limited to, a semiconductor memory, a magnetic memory, an optical memory, or the like. The memory 26 may function as, for example, a primary storage unit, an auxiliary storage unit, or a cache memory. The memory 26 stores any information to be used for an operation of the second terminal apparatus 15. The memory 26 may store, for example, a system program and an application program. The memory 26 may store identification information on the second terminal apparatus 15. The information stored in the memory 26 may be updated by using, for example, information received from the network 17 via the communication interface 22.

The controller 27 includes at least one processor. In the present embodiment, a "processor" is, but not limited to, a general processor or a processor especially for a particular processing operation. The controller 27 controls the entire operation of the second terminal apparatus 15.

When the communication interface 22 receives an operation plan described later, the controller 27 stores the operation plan in the memory 26. As used herein, the term "store" denotes storing information on a target such as an operation plan.

The operation plan includes a designated time, a stopover point, a final destination, and authentication information individually associated with the stopover point as information.

When an operation plan includes a plurality of stopover points, the designated time may be associated with a stopover point out of the stopover points. The designated time may be associated with, for example, a last stopover point of the stopover points. The designated time may be, for example, a time that precedes, by a buffer time, a scheduled medical service start time of the medical facility 16 associated with the first information processing apparatus 12. The buffer time is set to, for example, ten minutes after the arrival of the vehicle 10. During the buffer time, a physician can ride on the vehicle 10 and completes preparation of medical.

The stopover point may be, for example, a pickup location at which a physician determined by the medical facility 16 is picked up by the vehicle. The physician determined by the medical facility 16 is, for example, a physician belonging to the medical facility 16. The pickup location of a physician belonging to the medical facility 16 may be, for example, the place of residence of the physician. The physician determined by the medical facility 16 is, for example, a physician who proposes undertaking conditions matching recruiting conditions sent to the second information processing apparatus 14 as described later and who is determined by the medical facility 16 to be appointed. The pickup location of a physician determined by the medical facility 16 to be appointed may be, for example, a pickup location included in undertaking conditions.

The final destination may be, for example, a location of the medical facility 16 associated with the first information processing apparatus 12 or a location of a parking space designated by the medical facility 16.

In the case in which an operation plan includes a plurality of stopover points, the controller 27 recognizes a travel time from a first stopover point to a stopover point associated with a designated time. The travel time includes the total of a time for which the vehicle 10 actually moves and a time for which the vehicle 10 waits at each stopover point. In the case in which an operation plan includes a travel time, the controller 27 extracts and recognizes the travel time. Alternatively, in the case in which an operation plan does not include any travel time, the controller 27 calculates and recognizes a travel time. The controller 27 calculates a time to reach a first stopover point by subtracting a travel time from a designated time. The controller 27 stores the time to reach the first stopover point in the memory 26. In the case in which an operation plan includes a single stopover point, the controller 27 regards a designated time as a time to reach a first stopover point.

For example, the controller 27 cyclically receives a current location of the vehicle 10 from the location information acquisition apparatus 21. The controller 27 calculates a travel time from the current location to a first stopover point. The controller 27 calculates a departure time by subtracting a travel time from a time to reach the first stopover point. In the case in which the current time exceeds a time preceding a departure time by one cycle period used when a current location is received, the controller 27 generates control information for controlling the vehicle 10 to travel to a first stopover point and stops at the first stopover point. The controller 27 sends the control information to the control apparatus 19.

When a stopover point is reached, the controller 27 reads from the memory 26 authentication information associated with the stopover point. At the stopover point at which the vehicle stops, the controller 27 determines whether authentication information obtained from an individual to get in the vehicle is identical to the authentication information read from the memory 26.

The authentication information obtained from an individual to get in the vehicle may be a password assigned to the individual, information stored on a terminal apparatus of the individual, biological information on the individual, or the like. The biological information is, for example, information about an appearance unique to a person, such as a fingerprint, a venous pattern, or a retinal pattern.

The authentication information may be obtained, for example, through short-distance wireless communication with the first terminal apparatus 13 via the communication interface 22, by inputting a password on an input device of the vehicle 10, by capturing an image of authentication information output on the first terminal apparatus 13 with the use of a camera of the vehicle 10 or the like, or by detecting biological information with the use of a sensor of the vehicle 10 or the like.

When both pieces of authentication information are identical to each other, the controller 27 generates control information for controlling the vehicle 10 to move to a subsequent destination and stop at the subsequent destination. In the case in which an operation plan includes a subsequent stopover point after a stopover point at which the vehicle currently stops, the subsequent destination is the subsequent stopover point. In this case, when an operation plan includes a plurality of stopover points, the controller 27 repeats generating control information for controlling the vehicle 10 to travel from a stopover point to another stopover point until the vehicle 10 finishes traveling via all the stopover points. In the case in which an operation plan does not include a subsequent stopover point after a stopover point at which the vehicle currently stops, the subsequent destination is the final destination. In this case, the controller 27 generates control information for controlling the vehicle 10 to travel from a single stopover point or a last stopover point to the final destination.

In this manner, the controller 27 generates control information for controlling the vehicle 10 to reach a stopover point by a designated time and then to travel to a final destination. As described above, when a designated time is associated with a last stopover point, the controller 27 generates control information for controlling the vehicle 10 to travel via a plurality of stopover points and consequently reach the last stopover point of the plurality of stopover points by the designated time. The controller 27 sends the generated control information to the control apparatus 19.

The controller 27 may determine whether a match of authentication information on an individual is established before picking up the individual by the vehicle, so as to use the matching result to decide whether to unlock a door of the vehicle 10.

The controller 27 causes the output interface 24 to output the first sound and/or the first subject image received by the communication interface 22. The controller 27 controls the communication interface 22 to send the second sound and the second subject image detected by the sensor 23 to the first information processing apparatus 12. The controller 27 controls the communication interface 22 to send a relative position detected by the input interface 25 in accordance with a user input to the first information processing apparatus 12.

Figure 4:
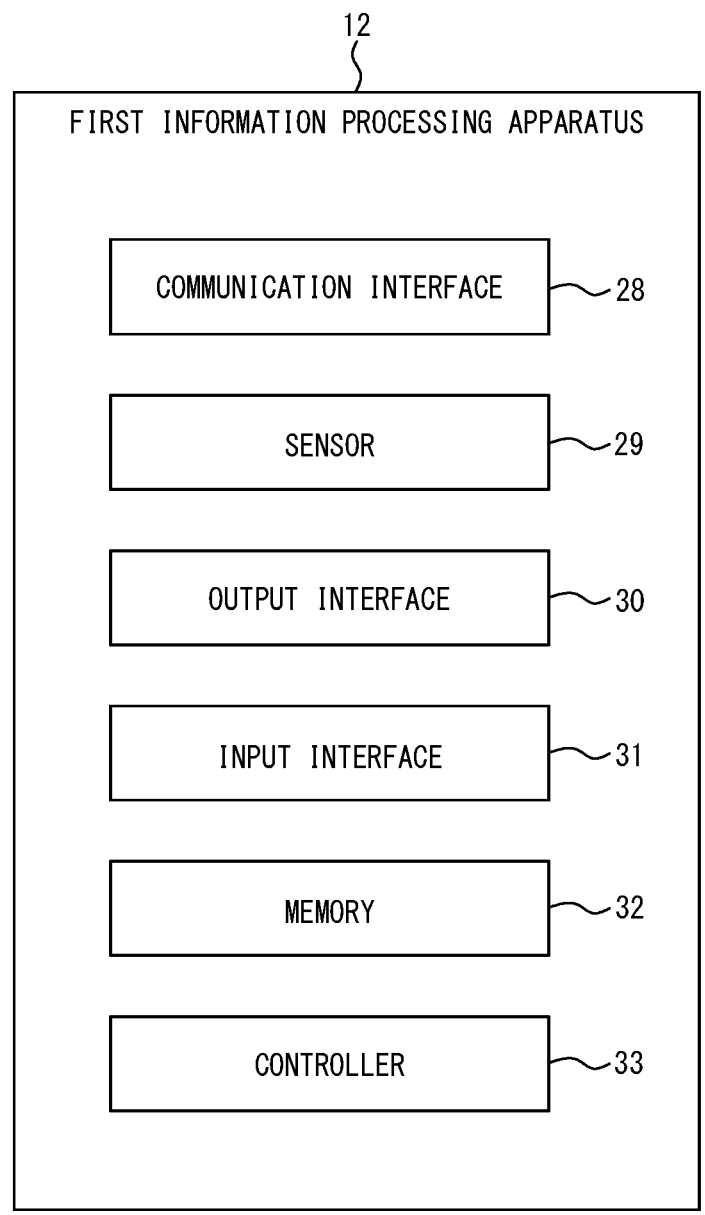
FIG. 4 is a functional block diagram schematically illustrating a configuration of a first information processing apparatus in FIG. 1.

As illustrated in FIG. 4, the first information processing apparatus 12 includes a communication interface 28, a sensor 29, an output interface 30, an input interface 31, a memory 32, and a controller 33. The first information processing apparatus 12 may include a plurality of the sensors 29. The plurality of the sensors 29 may be individually installed in a plurality of examination rooms especially for remote medical services. The first information processing apparatus 12 may include a plurality of the output interfaces 30. The plurality of the output interfaces 30 may be individually installed in the plurality of examination rooms especially for remote medical services.

The communication interface 28 includes a communication module configured to establish communication via a dedicated line. The communication interface 28 also includes a communication module configured to establish connection with the network 17. For example, the communication interface 28 may include a communication module compliant with mobile communication standards such as 4G and 5G. In the present embodiment, the first information processing apparatus 12 is connected to the network 17 via the communication interface 28. The communication interface 28 sends and receives various kinds of information via the network 17. When the communication interface 28 sends information through the network 17, the communication interface 28 may add identification information on the first information processing apparatus 12 to the information. The identification information on the first information processing apparatus 12 is information to be used for uniquely identifying the first information processing apparatus 12 in the information processing system 11.

The sensor 29 detects the first sound and/or the first subject image of a living body targeted for examination such as the body of a patient.

The sensor 29 includes, for example, a contact-type sound collection sensor such as a chest-piece microphone and detects sound at a part of a patient's body as the first sound while the sensor 29 is in direct contact with the part like a stethoscope. The first sound at a relative position is detected by detecting sound at the relative position while the contact-type sound collection sensor is in contact with the relative position output at the output interface 30 as described later.

The sensor 29 may include, for example, a wide-angle camera in which a position to be imaged is changeable and detect as the first subject image an enlarged image of a part of the surface of a living body. The sensor 29 may include, for example, an electronic endoscope in which a position to be imaged is changeable and detect as the first subject image a subject image of a lumen, such as the throat, that cannot be easily viewed under a room lamp. The first subject image at a relative position is detected by performing imaging in a state in which the wide-angle camera or the front end of an insertion tube of the electronic endoscope is directed toward the relative position output by the output interface 30 as described later.

The sensor 29 may include, for example, a sound collection sensor, such as a microphone, and receive sound in an examination room. The sensor 29 may include, for example, a camera fixed in an examination room and detect subject images in the examination room.

The output interface 30 includes at least one interface configured to output information to notify users. The output interface 30 includes, for example, a speaker configured to output information in the form of sound and outputs the second sound received by the communication interface 28 from the second terminal apparatus 15. The output interface 30 includes, for example, a display configured to output information in the form of image and outputs the second subject image and the relative position that are received by the communication interface 28 from the second terminal apparatus 15. The relative position is, for example, output in a viewable manner in which the relative position is indicated in a schematic drawing of an entire human body by a sign such as an arrow that indicates a position.

The input interface 31 includes at least one interface configured to detect user inputs. For example, the input interface 31 is, but not limited to, physical keys, capacitive keys, a touch screen provided in combination with a display of the output interface 30, or a microphone configured to accept sound input.

The memory 32 is, but not limited to, a semiconductor memory, a magnetic memory, an optical memory, or the like. The memory 32 may function as, for example, a primary storage unit, an auxiliary storage unit, or a cache memory. The memory 32 stores any information to be used for an operation of the first information processing apparatus 12. The memory 32 may store, for example, a system program and an application program. The memory 32 may store a name, the place of residence, and authentication information on a physician belonging to the medical facility 16 in an associated manner. The memory 32 may store reject conditions described later. The memory 32 may also store identification information on the first information processing apparatus 12. The information stored in the memory 32 may be updated by using, for example, information received from the network 17 via the communication interface 28.

The controller 33 includes at least one processor. In the present embodiment, a "processor" is, but not limited to, a general processor or a processor especially for a particular processing operation. The controller 33 controls the entire operation of the first information processing apparatus 12.

The controller 33 causes the output interface 30 to output the second sound, the second subject image, and a relative position received by the communication interface 28. The controller 33 controls the communication interface 28 to send to the second terminal apparatus 15 the first sound and/or the first subject image detected at the relative position by the sensor 29. The controller 33 controls the communication interface 28 to send to the second terminal apparatus 15 a sound in an examination room and a subject image in the examination room that are detected by the sensor 29.

The controller 33 generates an operation plan for the vehicle 10 managed by the medical facility 16. The controller 33 generates an operation plan including, for example, a designated time, a stopover point, a final destination, and authentication information individually associated with the stopover point.

For example, when a user input of a time by which the vehicle 10 needs to reach a stopover point is detected, the controller 33 may determine the time as a designated time and include the time in an operation plan. Alternatively, for example, the controller 33 may determine a preset time stored in the memory 32 as a designated time and include the preset time in an operation plan. As described above, the designated time may be set at, for example, a time that precedes, by a buffer time, a scheduled medical service start time of the medical facility 16, or a medical service available time for a physician after the scheduled medical service start time.

For example, when a user input for selecting from physicians registered in the memory 32 a particular physician to whom the vehicle 10 is to be dispatched is detected, the controller 33 may read the place of residence of the particular physician from the memory 32, determine the place of residence as a stopover point, and include the stopover point in an operation plan. Alternatively, for example, a user input of the place of residence of a physician to whom the vehicle 10 is to be dispatched is detected, the controller 33 may determine the place of residence as a stopover point and include the stopover point in an operation plan.

The controller 33 may determine as a stopover point a pickup location designated by a physician who is to provide a remote medical service by using the vehicle 10. The controller 33 determines the pickup location as a stopover point by following the operation described below.

For example, when the input interface 31 detects user inputs of recruiting conditions including a clinical department and a medical service request time, the controller 33 controls the communication interface 28 to send the recruiting conditions to the second information processing apparatus 14. The recruiting conditions are conditions required when the medical facility 16 seeks a physician who provides a remote medical service by using the vehicle 10. The medical service request time is a time for which providing a remote medical service by using the vehicle 10 is requested.

When, in response to the sent recruiting conditions, undertaking conditions matching the recruiting conditions are received from the second information processing apparatus 14, the controller 33 determines whether to appoint a physician sending the undertaking conditions. The undertaking conditions are conditions that a physician not belonging to the medical facility 16 can undertake when the physician provides a remote medical service by using the vehicle 10 as described later. The undertaking conditions include a clinical department, a medical service available time, and a pickup location by the vehicle 10 with respect to a physician.

For example, when undertaking conditions are received, the controller 33 causes the output interface 30 to output together with the undertaking conditions a request for a user input indicating whether to appoint a physician sending the undertaking conditions. When the input interface 31 detects a user input indicating whether to appoint a physician, the controller 33 decides whether to appoint the physician in accordance with the user input. The controller 33 controls the communication interface 28 to send a decision on appointment according to the user input as a determination result together with the undertaking conditions and the recruiting conditions to the second information processing apparatus 14.

Alternatively, for example, when undertaking conditions are detected, the controller 33 reads reject conditions from the memory 32 and determines whether the undertaking conditions match the reject conditions. The reject conditions are conditions of physicians whom the medical facility 16 rejects to provide remote medical services by using the vehicle 10. The reject conditions can be set by the medical facility 16. The reject conditions are, for example, an individual name of a specific physician and a pickup location apart from a location of the medical facility 16 by a distance equal to or greater than a threshold. The controller 33 determines whether to appoint a particular physician by comparing undertaking conditions and reject conditions. In the case in which the undertaking conditions do not match the reject conditions, the controller 33 controls the communication interface 28 to send, to the second information processing apparatus 14, a decision on appointment indicating that the particular physician is appointed, together with the undertaking conditions and the recruiting conditions. In the case in which the undertaking conditions match the reject conditions, the controller 33 controls the communication interface 28 to send to the second information processing apparatus 14 a decision on appointment indicating that the particular physician is rejected.

The controller 33 controls the communication interface 28 to send to the second information processing apparatus 14, together with a decision on appointment indicating that a particular physician is appointed, a name of the medical facility 16 and an arrival time at which the vehicle 10 is expected to arrive at a pickup location included in undertaking conditions. The arrival time of the vehicle 10 is, for example, a designated time.

When a decision on appointment indicating that a particular physician is appointed is sent as described above, the controller 33 determines a pickup location included in undertaking conditions as a stopover point and includes the stopover point in an operation plan.

The controller 33 may determine a plurality of stopover points in accordance with user inputs via the input interface 31 and/or received undertaking conditions and include the stopover points in an operation plan. When a plurality of stopover points are determined, the controller 33 may cause the output interface 30 to output a request to associate a designated time with any of the stopover points. When a user input for associating a designated time with a particular stopover point is detected, the controller 33 associates the designated time with a particular stopover point in accordance with the user input.

Together with determining a stopover point, the controller 33 determines authentication information to be individually associated with a stopover point. In the case in which a stopover point indicates an address of a physician belonging to the medical facility 16, the controller 33 reads authentication information associated with the physician from the memory 32. The controller 33 determines the read authentication information as authentication information to be associated with the stopover point and includes the authentication information in an operation plan. In the case in which a stopover point is a pickup location included in undertaking conditions, the controller 33 generates new authentication information, determines the new authentication information as authentication information to be associated with the stopover point, and includes the authentication information in an operation plan. The controller 33 controls the communication interface 28 to send the generated authentication information to the second information processing apparatus 14.

For example, in the case in which a user input of a destination of the vehicle 10 is detected, the controller 33 may include the destination as a final destination in an operation plan. Alternatively, for example, the controller 33 may include a preset location stored in the memory 32 as a final destination in an operation plan. As described above, the final destination may be, for example, a location of the medical facility 16 or a location of a parking space designated by the medical facility 16. The parking space may be, for example, a parking space in a suburb or the like and may be a parking space for which the medical facility 16 has a contract.

The controller 33 controls the communication interface 28 to send an operation plan generated by including a designated time, a stopover point, a final destination, and authentication information individually associated with the stopover point to the second terminal apparatus 15 installed in the vehicle 10 managed by the medical facility 16.

Figure 5:
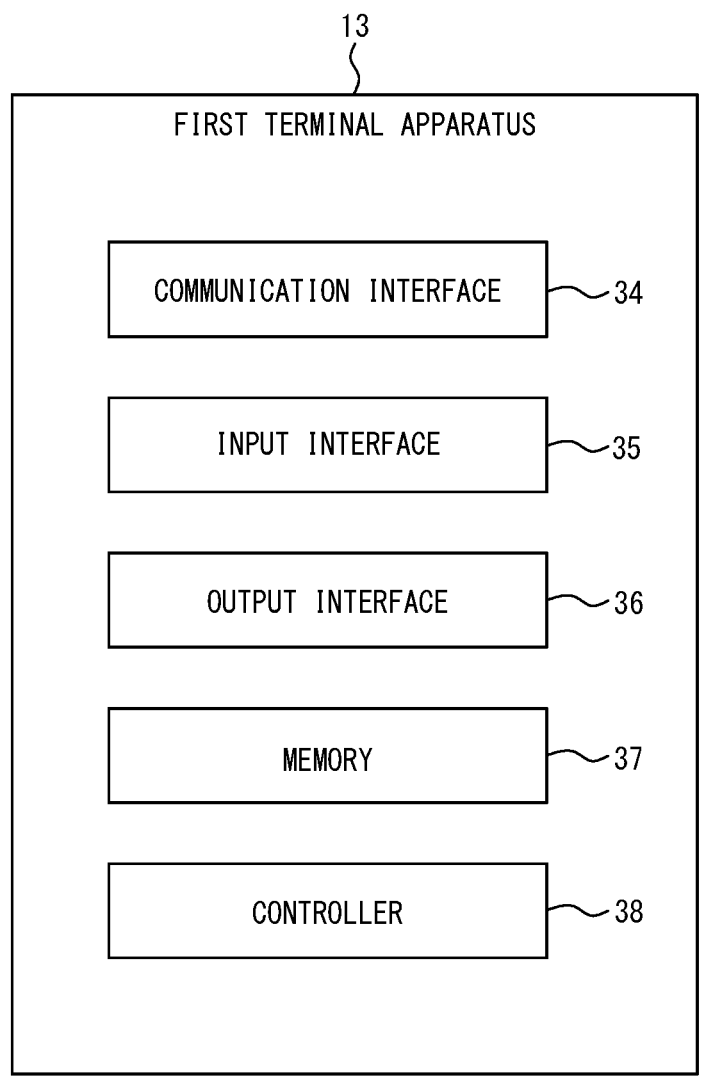
FIG. 5 is a functional block diagram schematically illustrating a configuration of a first terminal apparatus in FIG. 1.

As illustrated in FIG. 5, the first terminal apparatus 13 includes a communication interface 34, an input interface 35, an output interface 36, a memory 37, and a controller 38.

The communication interface 34 includes a communication module configured to establish connection with the network 17. For example, the communication interface 34 may include a communication module compliant with mobile communication standards such as 4G and 5G. For example, the communication interface 34 may include a communication module compliant with a short-distance wireless communication standard such as Bluetooth©. In the present embodiment, the first terminal apparatus 13 is connected to the network 17 via the communication interface 34. The communication interface 34 sends and receives various kinds of information via the network 17. When the communication interface 34 sends information through the network 17, the communication interface 34 may add identification information on the first terminal apparatus 13 to the information. The identification information on the first terminal apparatus 13 is information to be used for uniquely identifying the first terminal apparatus 13 in the information processing system 11.

The input interface 35 includes at least one interface configured to detect user inputs. For example, the input interface 35 is, but not limited to, physical keys, capacitive keys, a touch screen provided in combination with a display of the output interface 36, or a microphone configured to accept sound input.

The output interface 36 includes at least one interface configured to output information to notify users. For example, the output interface 36 is, but not limited to, a display configured to output information as an image or a speaker configured to output information in sound.

The memory 37 is, but not limited to, a semiconductor memory, a magnetic memory, an optical memory, or the like. The memory 37 may function as, for example, a primary storage unit, an auxiliary storage unit, or a cache memory. The memory 37 stores any information to be used for an operation of the first terminal apparatus 13. The memory 37 may store, for example, a system program and an application program. The memory 37 may store identification information on the first terminal apparatus 13. The information stored in the memory 37 may be updated by using, for example, information received from the network 17 via the communication interface 34.

The controller 38 includes at least one processor. In the present embodiment, a "processor" is, but not limited to, a general processor or a processor especially for a particular processing operation. The controller 38 controls the entire operation of the first terminal apparatus 13.

For example, when the input interface 35 detects user inputs of undertaking conditions including a clinical department, a medical service available time, and a pickup location, the controller 38 controls the communication interface 34 to send the undertaking conditions to the second information processing apparatus 14. The undertaking conditions are conditions that an owner of the first terminal apparatus 13 such as a physician can undertake when the physician provides a remote medical service by using the vehicle 10. The medical service available time is a time for which the owner can provide medical services in the vehicle 10; in the present embodiment, the medical service available time additionally includes a time it takes to ride on the vehicle. The pickup location is a location at which the owner can arrive by a start time of a medical service available time and may be, for example, the place of residence of the owner.

When a notification of appointment is received from the second information processing apparatus 14 in response to sending of undertaking conditions, the controller 38 causes the output interface 36 to output the notification of appointment. The notification of appointment includes a name of the medical facility 16 that appoints a physician to provide a remote medical service by using the vehicle 10, an arrival time at which the vehicle 10 is expected to arrive at a pickup location, authentication information, and the like. The controller 38 stores the authentication information in the memory 37.

When authentication information is requested by the second terminal apparatus 15 via the communication interface 34 through short-distance wireless communication, the controller 38 reads authentication information from the memory 37 and controls the communication interface 34 to send the authentication information to the second terminal apparatus 15. Alternatively, when the input interface 35 detects a user input of a request to output authentication information, the controller 38 reads authentication information from the memory 37 and causes the output interface 36 to output the authentication information.

Figure 6:
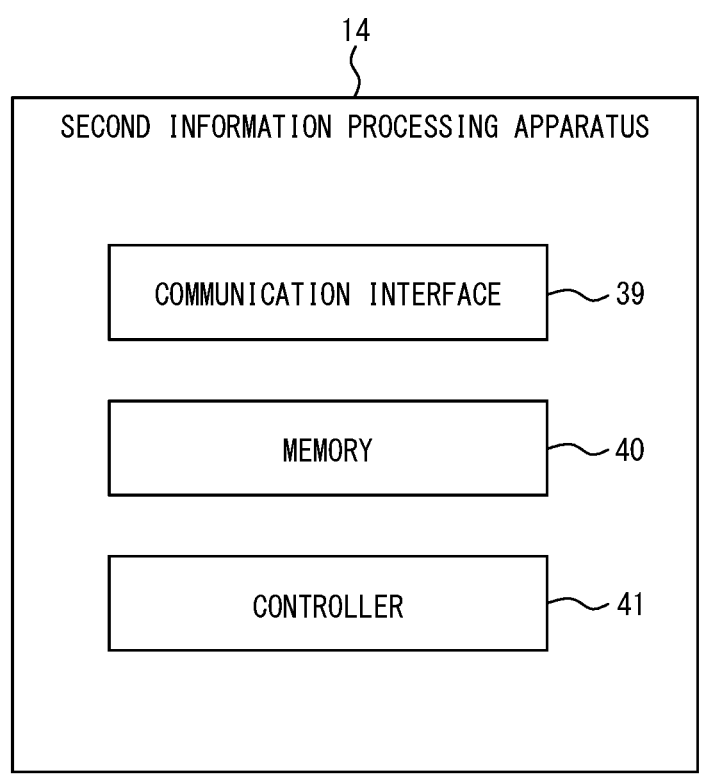
FIG. 6 is a functional block diagram schematically illustrating a configuration of a second information processing apparatus in FIG. 1.

As illustrated in FIG. 6, the second information processing apparatus 14 includes a communication interface 39, a memory 40, and a controller 41.

The communication interface 39 includes a communication module configured to establish communication via a dedicated line. The communication interface 39 also includes a communication module configured to establish connection with the network 17. For example, the communication interface 39 may include a communication module compliant with mobile communication standards such as 4G and 5G. In the present embodiment, the second information processing apparatus 14 is connected to the network 17 via the communication interface 39. The communication interface 39 sends and receives various kinds of information via the network 17. When the communication interface 39 sends information through the network 17, the communication interface 39 may add identification information on the second information processing apparatus 14 to the information. The identification information on the second information processing apparatus 14 is information to be used for uniquely identifying the second information processing apparatus 14 in the information processing system 11.

The memory 40 is, but not limited to, a semiconductor memory, a magnetic memory, an optical memory, or the like. The memory 40 may function as, for example, a primary storage unit, an auxiliary storage unit, or a cache memory. The memory 40 stores any information to be used for an operation of the second information processing apparatus 14. The memory 40 may store, for example, a system program and an application program.

The controller 41 includes at least one processor. In the present embodiment, a "processor" is, but not limited to, a general processor or a processor especially for a particular processing operation. The controller 41 controls the entire operation of the second information processing apparatus 14.

When recruiting conditions are received from the first information processing apparatus 12, the controller 41 stores in the memory 40 the recruiting conditions in association with the first information processing apparatus 12. When undertaking conditions are received from the first terminal apparatus 13, the controller 41 stores in the memory 40 the undertaking conditions in association with the first terminal apparatus 13.

The controller 41 checks, for example, regularly or cyclically whether particular undertaking conditions stored in the memory 40 match any recruiting conditions stored in the memory 40. The state in which undertaking conditions match recruiting conditions denotes that a clinical department of the undertaking conditions is identical to a clinical department of the recruiting conditions and a medical service available time included in the undertaking conditions involves a medical service request time included in the recruiting conditions. When particular undertaking conditions match particular recruiting conditions, the controller 41 controls the communication interface 39 to send the particular undertaking conditions to the first information processing apparatus 12 associated with the particular recruiting conditions.

Alternatively, when particular recruiting conditions are received, the controller 41 checks whether any undertaking conditions out of undertaking conditions stored in the memory 40 match the particular recruiting conditions. When particular undertaking conditions match the particular recruiting conditions, the controller 41 controls the communication interface 39 to send the discovered particular undertaking conditions to the first information processing apparatus 12 associated with the particular recruiting conditions.

Alternatively, when particular undertaking conditions are received, the controller 41 checks whether any recruiting conditions out of recruiting conditions stored in the memory 40 match the particular undertaking conditions. When particular recruiting conditions match the particular undertaking conditions, the controller 41 controls the communication interface 39 to send the particular undertaking conditions to the first information processing apparatus 12 associated with the particular recruiting conditions.

When a decision on appointment indicating that a physician is appointed is received from the first information processing apparatus 12 in response to sending undertaking conditions to the first information processing apparatus 12, the controller 41 excludes the undertaking conditions received together with the decision on appointment from being a target for determining whether to match any recruiting conditions from this point forward. This means that the controller 41 excludes the undertaking conditions from being a target to be sent to the first information processing apparatus 12 in response to recruiting conditions from this point forward. The controller 41 also excludes the recruiting conditions received together with a decision on appointment from being a target for determining whether to match any undertaking conditions from this point forward.

When a decision on appointment indicating that a physician is appointed is received from the first information processing apparatus 12 in response to sending undertaking conditions to the first information processing apparatus 12, the controller 41 generates a notification of appointment. The notification of appointment includes a name of the medical facility 16 that decides to appoint a physician to provide a remote medical service by using the vehicle 10, an arrival time at which the vehicle 10 is expected to arrive at a pickup location included in undertaking conditions, and authentication information. The controller 41 generates a notification of appointment by, for example, associating a name of the medical facility 16 and an arrival time at which the vehicle 10 is expected to arrive at a pickup location, which are received together with a decision on appointment, and authentication information with each other. The controller 41 controls the communication interface 39 to send the notification of appointment to the first terminal apparatus 13 sending the undertaking conditions.

Figure 7:
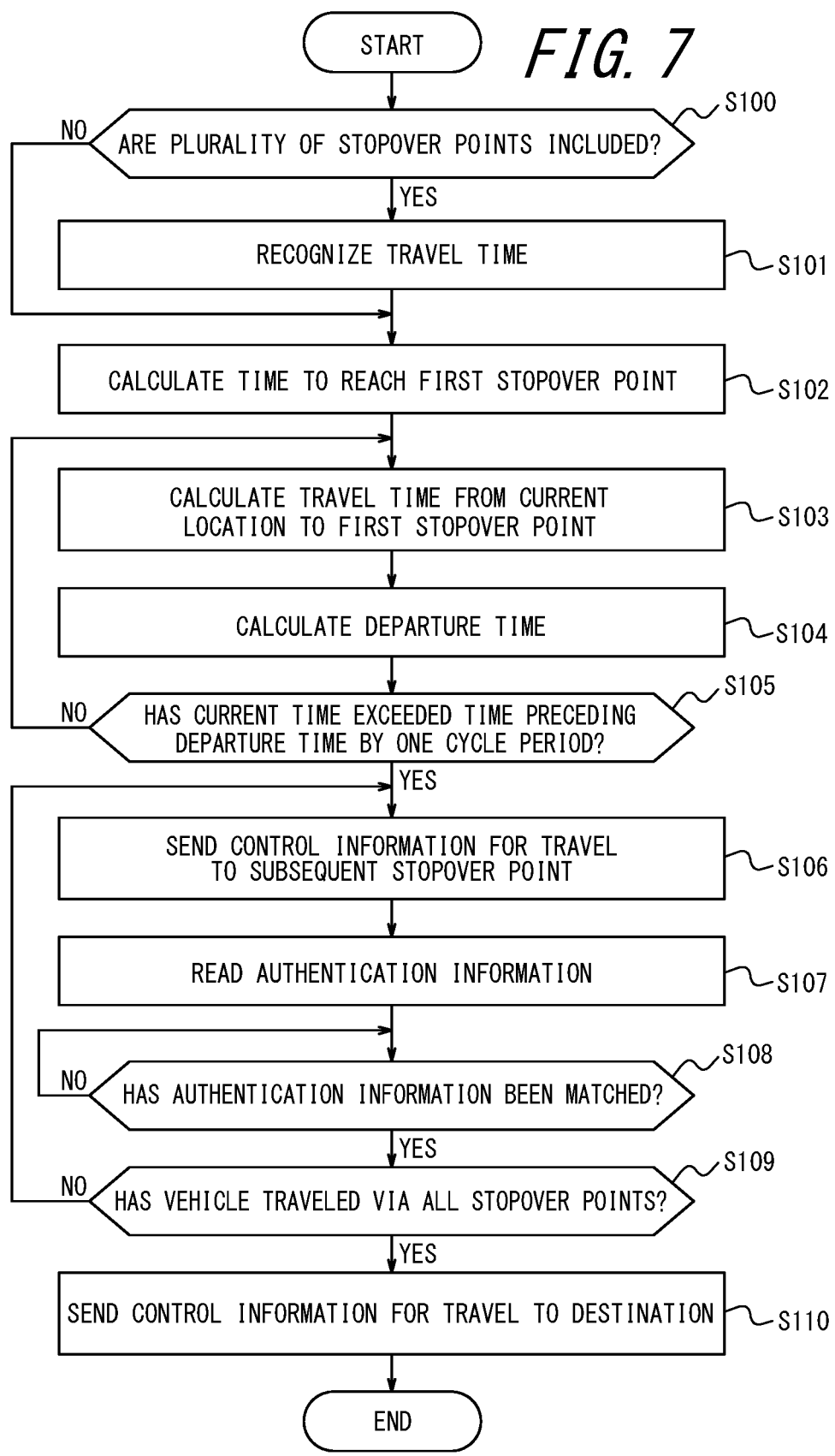
FIG. 7 is a flowchart illustrating control information generation processing performed by a controller in FIG. 3.

Next, control information generation processing performed by the controller 27 of the second terminal apparatus 15 in the present embodiment is described with reference to a flowchart in FIG. 7. The control information generation processing is started when, for example, the communication interface 22 receives an operation plan sent by the first information processing apparatus 12.

In step S100, the controller 27 determines whether the received operation plan includes a plurality of stopover points. In the case in which a plurality of stopover points are included, the process proceeds to step S101. In the case in which a plurality of stopover points are not included, the process proceeds to step S102.

In step S101, the controller 27 recognizes a travel time from a first stopover point in the operation plan to a stopover point associated with a designated time. After the travel time is recognized, the process proceeds to step S102.

In step S102, the controller 27 calculates a time to reach the first stopover point by subtracting the travel time recognized in step S101 from the designated time included in the operation plan. After the time is calculated, the process proceeds to step S103.

In step S103, the controller 27 calculates a travel time from a current location of the vehicle 10 cyclically received from the location information acquisition apparatus 21 to the first stopover point included in the operation plan. After the travel time is calculated, the process proceeds to step S104.

In step S104, the controller 27 calculates a departure time by subtracting the travel time calculated in step S103 from the time to reach the first stopover point calculated in step S102. After the departure time is calculated, the process proceeds to step S105.

In step S105, the controller 27 determines whether a current time exceeds a time preceding the departure time calculated in step S104 by one cycle period used for measuring a current location. In the case in which the current time does not exceed the time, the process returns to step S103. In the case in which the current time exceeds the time, the process proceeds to step S106.

In step S106, the controller 27 generates control information for controlling the vehicle to travel from the current location to a subsequent stopover point and stop at the stopover point. The controller 27 controls the communication interface 22 to send the generated control information to the control apparatus 19. After the control information is sent, the process proceeds to step S107.

In step S107, the controller 27 reads from the memory 26 authentication information associated with the stopover point in the control information generated in step S106. After the authentication information is read, the process proceeds to step S108.

In step S108, the controller 27 determines whether the authentication information read in step S107 is identical to authentication information detected with regard to an individual who is to get in the vehicle at the stopover point in the control information generated in step S106 or authentication information detected with regard to or received from the first terminal apparatus 13 carried by the individual. In the case in which both are not identical to each other, the process returns to step S108. In the case in which both are identical to each other, the process proceeds to step S109.

In step S109, the controller 27 determines whether the vehicle has traveled via all stopover points included in the operation plan. In the case in which the vehicle has not travelled via all the stopover points, the process returns to step S106. In the case in which the vehicle has travelled via all the stopover points, the process proceeds to step S110.

In step S110, the controller 27 generates control information for controlling the vehicle to travel to a final destination included in the operation plan. The controller 27 sends the generated control information to the control apparatus 19. After the control information is sent, the control information generation processing is ended.

Figure 8:
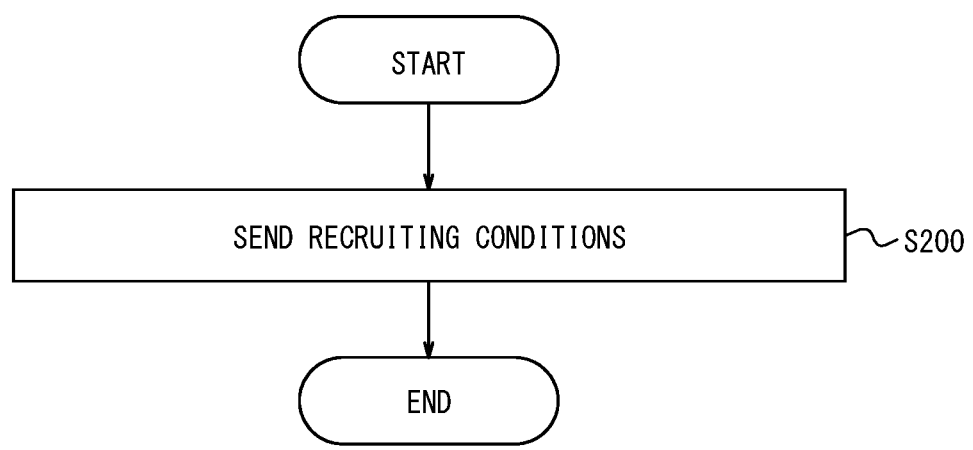
FIG. 8 is a flowchart illustrating recruiting processing performed by a controller in FIG. 4.

Next, recruiting processing performed by the controller 33 of the first information processing apparatus 12 in the present embodiment is described with reference to a flowchart in FIG. 8. The recruiting processing is started when, for example, user inputs of recruiting conditions are detected.

In step S200, the controller 33 controls the communication interface 28 to send to the second information processing apparatus 14 the recruiting conditions of the detected user inputs. After the recruiting conditions are sent, the recruiting processing is ended.

Figure 9:
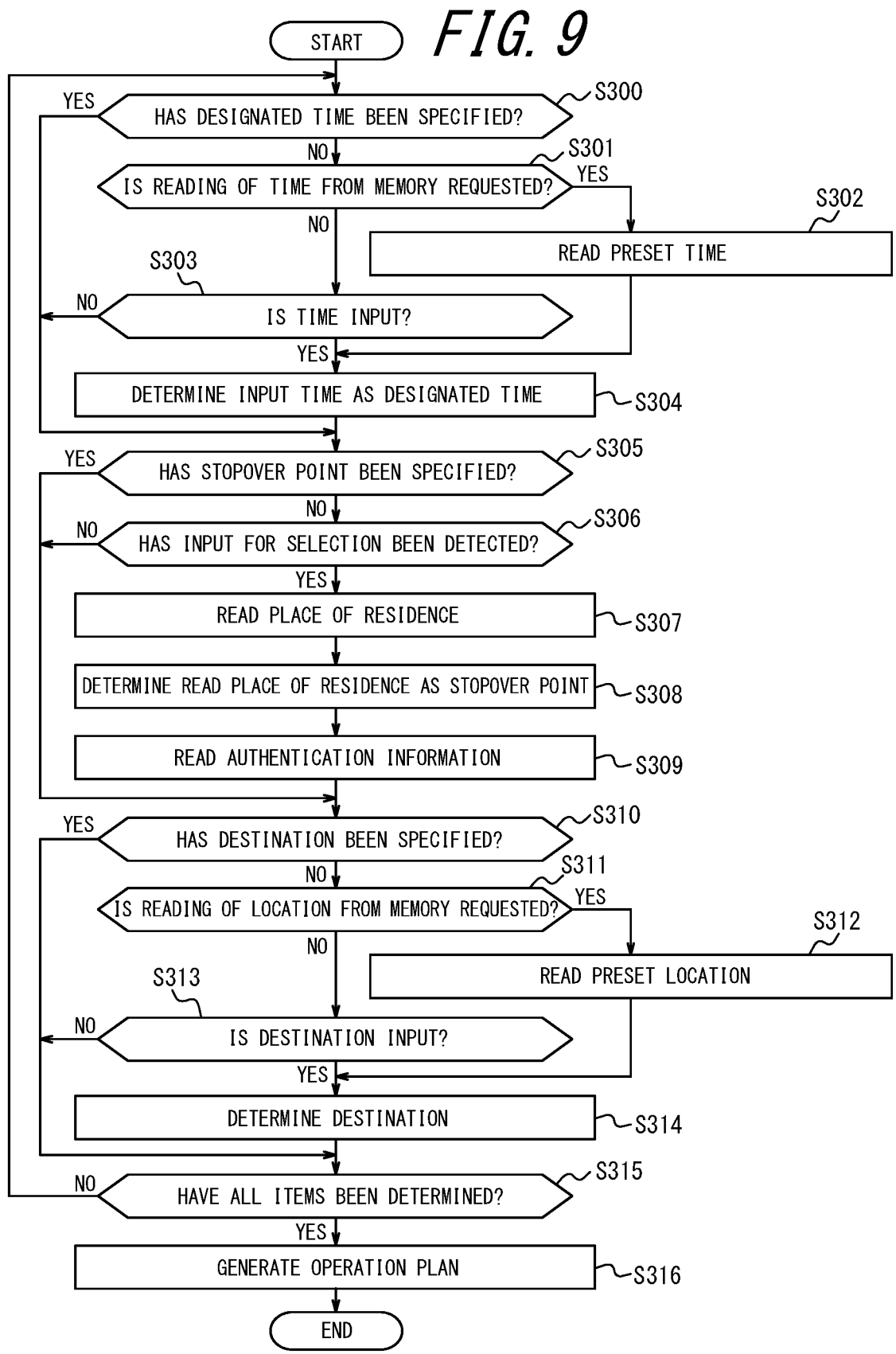
FIG. 9 is a flowchart illustrating first operation plan generation processing performed by the controller in FIG. 4.

Next, first operation plan generation processing performed by the controller 33 of the first information processing apparatus 12 in the present embodiment is described with reference to a flowchart in FIG. 9. The first operation plan generation processing is started when, for example, a user input of a request to generate an operation plan for a physician belonging to the medical facility 16 is detected.

In step S300, the controller 33 determines whether a designated time to be included in the operation plan is specified. In the case in which a designated time is specified, the process proceeds to step S305. In the case in which no designated time is specified, the process proceeds to step S301.

In step S301, the controller 33 determines whether the input interface 31 detects a user input of a request to read a preset time from the memory 32. In the case in which the user input is detected, the process proceeds to step S302. In the case in which the user input is not detected, the process proceeds to step S303.

In step S302, the controller 33 reads a preset time from the memory 32. After a preset time is read, the process proceeds to step S304.

In step S303, the controller 33 determines whether the input interface 31 detects a user input of a time at which the vehicle 10 is controlled to reach a stopover point. In the case in which the user input is not detected, the process proceeds to step S305. In the case in which the user input is detected, the process proceeds to step S304.

In step S304, the controller 33 determines as a designated time the time read in step S302 or the time of the user input checked in step S303. After a designated time is determined, the process proceeds to step S305.

In step S305, the controller 33 determines whether a stopover point to be included in the operation plan is specified. In the case in which a stopover point is specified, the process proceeds to step S310. In the case in which no stopover point is specified, the process proceeds to step S306.

In step S306, the controller 33 determines whether the input interface 31 detects a user input for selecting a physician. In the case in which no user input for selecting a physician is detected, the process proceeds to step S310. In the case in which the user input for selecting a physician is detected, the process proceeds to step S307.

In step S307, the controller 33 reads, from the memory 32, the place of residence of the physician who is determined in step S306 to be selected. After the place of residence is read, the process proceeds to step S308.

In step S308, the controller 33 determines the place of residence read in step S307 as a stopover point. After the stopover point is determined, the process proceeds to step S309.

In step S309, the controller 33 reads from the memory 32 authentication information associated with the physician who is determined in step S306 to be selected. After the authentication information is read, the process proceeds to step S310.

In step S310, the controller 33 determines whether a final destination to be included in the operation plan is specified. In the case in which a final destination is specified, the process proceeds to step S315. In the case in which no final destination is specified, the process proceeds to step S311.

In step S311, the controller 33 determines whether the input interface 31 detects a user input of a request to read a preset location from the memory 32. In the case in which the user input is detected, the process proceeds to step S312. In the case in which the user input is not detected, the process proceeds to step S313.

In step S312, the controller 33 reads a preset location from the memory 32. After a preset location is read, the process proceeds to step S314.

In step S313, the controller 33 determines whether the input interface 31 detects a user input of a final destination of the vehicle 10. In the case in which the user input is not detected, the process proceeds to step S315. In the case in which the user input is detected, the process proceeds to step S314.

In step S314, the controller 33 determines as a final destination the location read in step S312 or the destination of the user input checked in step S303. After the final destination is determined, the process proceeds to step S315.

In step S315, the controller 33 determines whether items of a designated time, a stopover point, and a final destination to be included in the operation plan have been all determined. In the case in which not all the items have been determined, the process returns to step S300. In the case in which all the items have been determined, the process proceeds to step S316.

In step S316, the controller 33 generates the operation plan including the designated time determined in step S304, the stopover point determined in step S308, the authentication information read in step S309, and the final destination determined in step S314. The controller 33 controls the communication interface 28 to send the generated operation plan to the vehicle 10. After the operation plan is sent, the first operation plan generation processing is ended.

Figure 10:
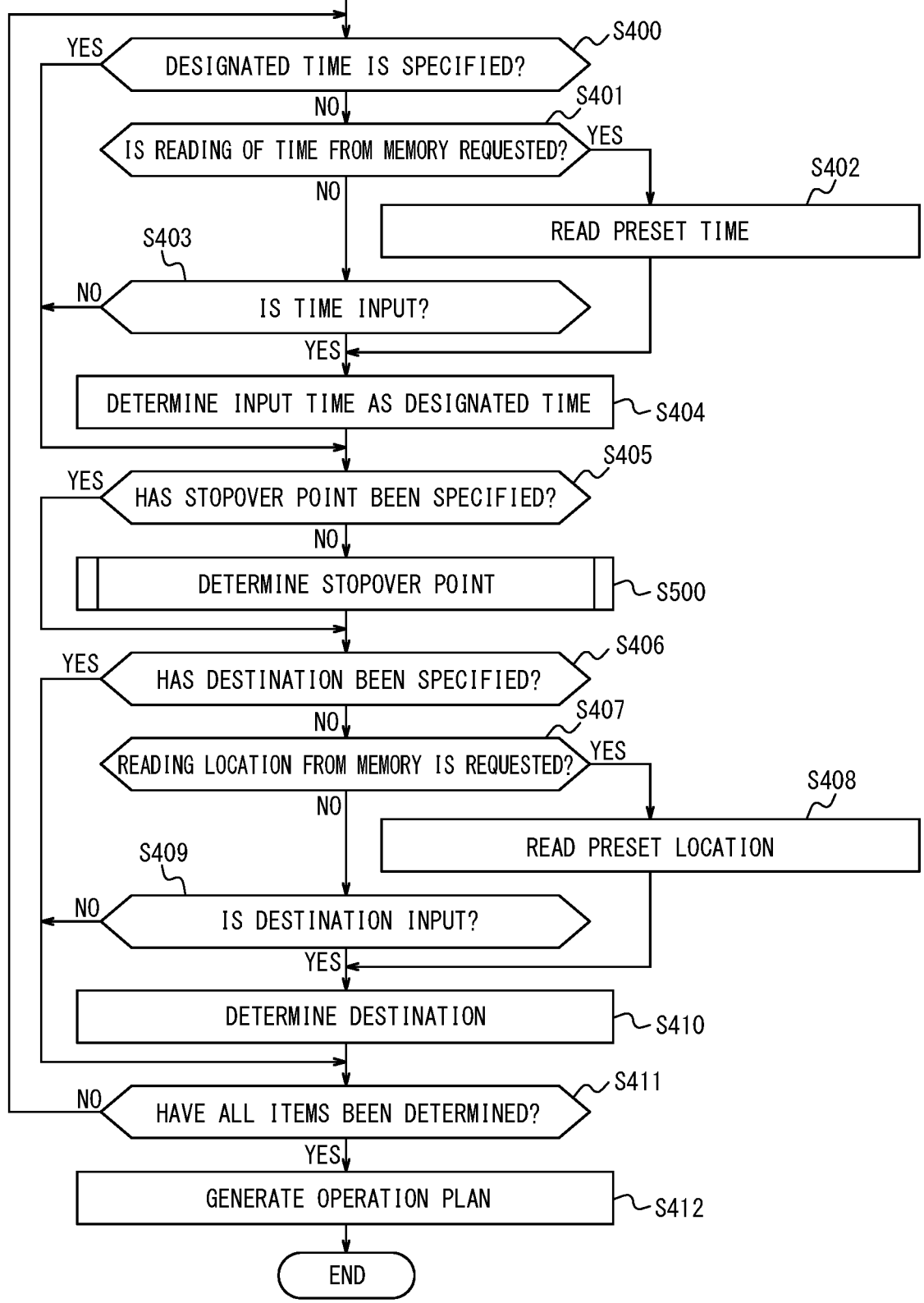
FIG. 10 is a flowchart illustrating second operation plan generation processing performed by the controller in FIG. 4.

Next, second operation plan generation processing performed by the controller 33 of the first information processing apparatus 12 in the present embodiment is described with reference to a flowchart in FIG. 10. The second operation plan generation processing is started when, for example, after recruiting conditions are sent, a user input of a request to generate an operation plan is detected.

In steps S400 to S405, the controller 33 performs control operations identical to the control operations in steps S300 to S305 of the first operation plan generation processing. In the case in which a stopover point is determined to have been specified in step S405, the process proceeds to step S406. In the case in which no stopover point is determined to have been specified in step S405, the process proceeds to step S500 and in the step S500 the controller 33 performs stopover point determination subroutine processing as described later. After the stopover point determination subroutine processing is performed, the process proceeds to step S406.

In steps S406 to S412, the controller 33 performs control operations identical to the control operations in steps S310 to S316 of the first operation plan generation processing. After the operation plan is sent in step S412, the second operation plan generation processing is ended.

Figure 11:
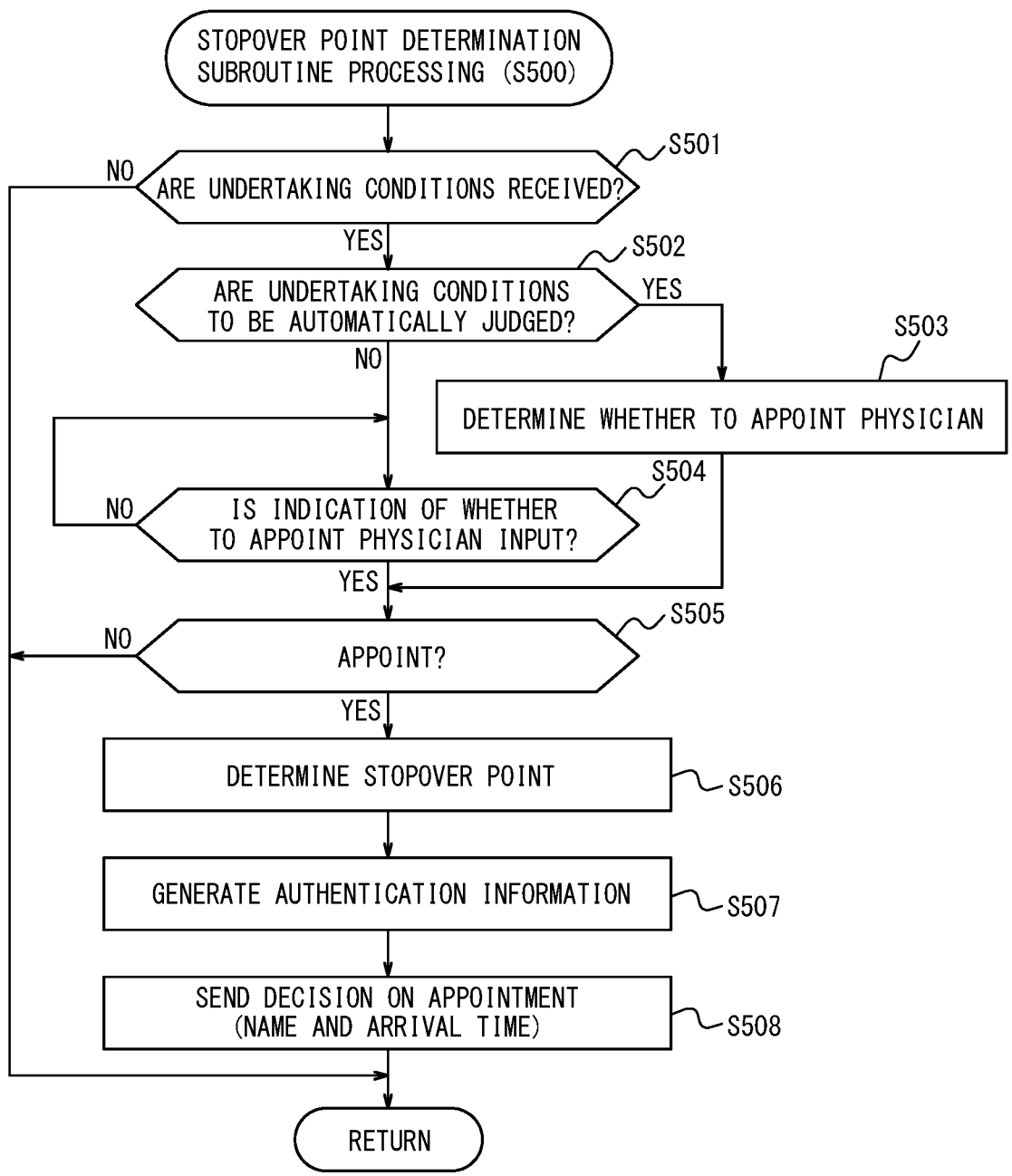
FIG. 11 is a flowchart illustrating stopover point determination subroutine processing performed by the controller in FIG. 4.

Next, the stopover point determination subroutine processing performed by the controller 33 of the first information processing apparatus 12 in the present embodiment is described with reference to a flowchart in FIG. 11.

In step S501, the controller 33 determines whether the communication interface 28 receives from the second information processing apparatus 14 undertaking conditions matching recruiting conditions that have been sent. In the case in which no undertaking conditions are received, the stopover point determination subroutine processing is ended and the process returns to step S406 of the second operation plan generation processing (refer to FIG. 11). In the case in which undertaking conditions are received, the process proceeds to step S502.

In step S502, the controller 33 determines whether undertaking conditions are to be automatically judged. The settings of automatic judgment of undertaking conditions can be switched between ON and OFF in accordance with, for example, a user input for switching via the input interface 31 of the first information processing apparatus 12. In the case in which automatic judgment is set, the process proceeds to step S503. In the case in which no automatic judgment is set, the process proceeds to step S504.

In step S503, the controller 33 reads reject conditions from the memory 32. The controller 33 determines, in accordance with the read reject conditions, whether to appoint a physician of the undertaking conditions determined in step S501 to have been received. After the determination is made, the process proceeds to step S505.

In step S504, the controller 33 causes the output interface 30 to output a request for a user input indicating whether to appoint a physician. The controller 33 determines whether the input interface 31 has detected a user input indicating whether a physician is appointed. In the case in which the user input has not been detected, the process returns to step S504 and the controller 33 waits until the user input is detected. In the case in which the user input has been detected, the process proceeds to step S505.

In step S505, in accordance with the determination result in step S303 or the user input checked in step S304, the controller 33 determines whether to appoint a physician sending undertaking conditions. In the case in which the physician is determined not to be appointed, the stopover point determination subroutine processing is ended and the process returns to step S406 of the second operation plan generation processing (refer to FIG. 11). In the case in which the physician is determined to be appointed, the process proceeds to step S506.

In step S506, the controller 33 determines a pickup location included in the undertaking conditions as a stopover point. After the stopover point is determined, the process proceeds to step S507.

In step S507, the controller 33 generates authentication information. After the authentication information is generated, the process proceeds to step S508.

In step S508, in accordance with the determination result in step S503 or the user input checked in step S504, the controller 33 generates a decision on appointment indicating whether to appoint a physician. The controller 33 controls the communication interface 28 to send the generated decision on appointment, to the second information processing apparatus 14. After the decision on appointment is sent, the stopover point determination subroutine processing is ended and the process returns to step S406 of the second operation plan generation processing (refer to FIG. 11).

Figure 12:
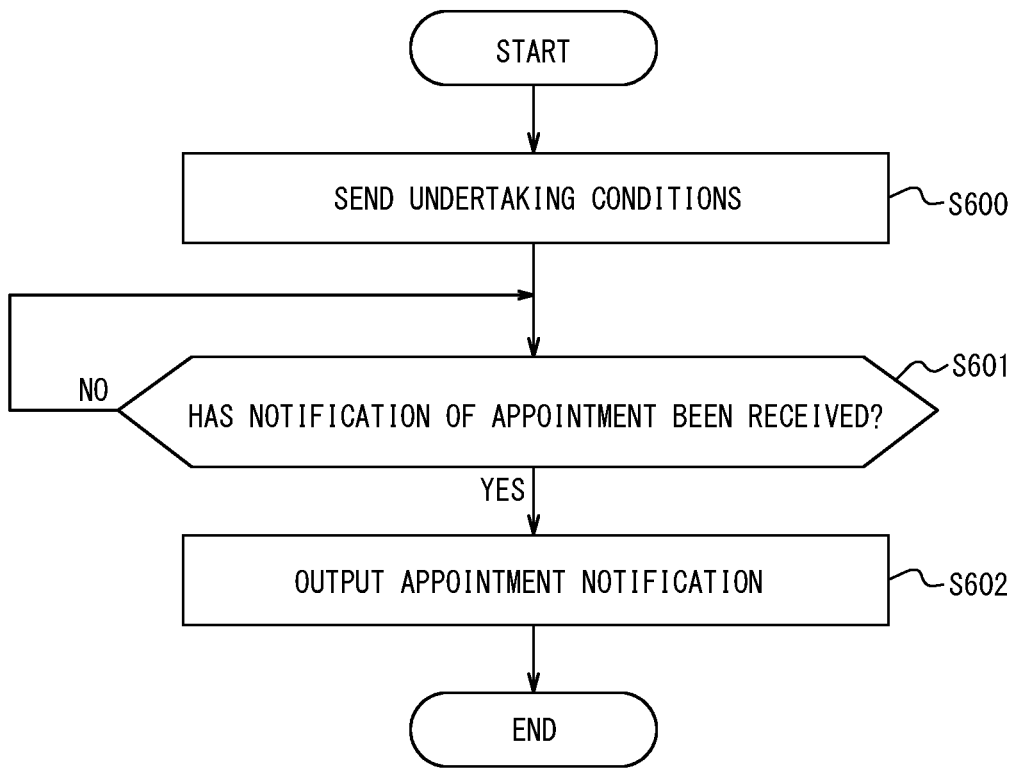
FIG. 12 is a flowchart illustrating job application processing performed by a controller in FIG. 5.

Next, job application processing performed by the controller 38 of the first terminal apparatus 13 in the present embodiment is described with reference to a flowchart in FIG. 12. The job application processing is started when, for example, the input interface 35 detects user inputs of undertaking conditions.

In step S600, the controller 38 controls the communication interface 34 to send the undertaking conditions of the user inputs to the second information processing apparatus 14. After the undertaking conditions are sent, the process proceeds to step S601.

In step S601, the controller 38 determines whether the communication interface 34 has received a notification of appointment in response to the undertaking conditions sent in step S600. In the case in which no notification of appointment has been received, the process returns to step S601. In the case in which a notification of appointment has been received, the process proceeds to step S602.

In step S602, the controller 38 stores, in the memory 37, the notification of appointment determined in step S601 as have been received. The controller 38 causes the output interface 36 to output the notification of appointment. After the notification of appointment is output, the job application processing is ended.

Figure 13:
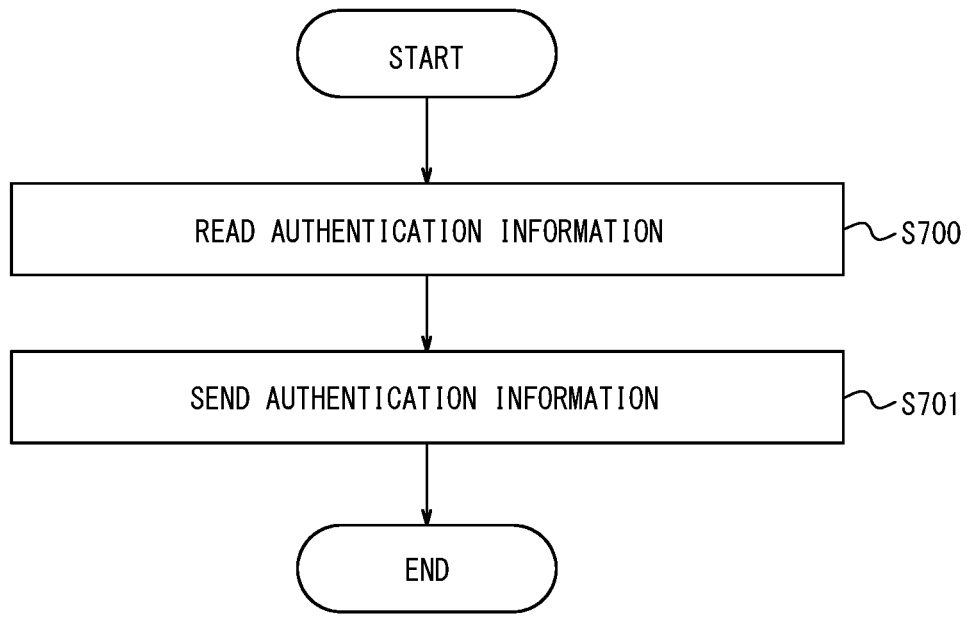
FIG. 13 is a flowchart illustrating authentication information presentation processing performed by the controller in FIG. 5.

Next, authentication information presentation processing performed by the controller 38 of the first terminal apparatus 13 in the present embodiment is described with reference to a flowchart in FIG. 13. The authentication information presentation processing is started when, for example, authentication information is requested by the second terminal apparatus 15 through short-distance wireless communication.

In step S700, the controller 38 reads authentication information from the memory 37. After authentication information is read, the process proceeds to step S701.

In step S701, the controller 38 controls the communication interface 34 to send the authentication information read in step S700 to the second terminal apparatus 15 through short-distance wireless communication. After the authentication information is sent, the authentication information presentation processing is ended.

Next, matching processing performed by the controller 41 of the second information processing apparatus 14 in the present embodiment is described with reference to a flowchart in FIG. 14. The matching processing is, for example, cyclically started.

In step S800, the controller 41 reads unmatched recruiting conditions from the memory 40. The unmatched recruiting conditions are recruiting conditions other than the recruiting conditions received from the first information processing apparatus 12 together with a decision on appointment indicating that a physician is appointed. After unmatched recruiting conditions are read, the process proceeds to step S801.

In step S801, the controller 41 reads unmatched undertaking conditions from the memory 40. The unmatched undertaking conditions are undertaking conditions other than the undertaking conditions received from the first information processing apparatus 12 together with a decision on appointment indicating that a physician is appointed. After unmatched undertaking conditions are read, the process proceeds to step S802.

In step S802, the controller 41 determines whether the undertaking conditions read in step S801 match the recruiting conditions read in step S800. In the case in which the undertaking conditions do not match the recruiting conditions, the process proceeds to step S803. In the case in which the undertaking conditions match the recruiting conditions, the process proceeds to step S804.

In step S803, the controller 41 determines whether unmatched undertaking conditions in the memory 40 have been all checked with regard to whether to match any recruiting conditions. In the case in which not all the unmatched undertaking conditions have been checked, the process returns to step S801. In the case in which all the unmatched undertaking conditions have been checked, the process proceeds to step S805.

In step S804, the controller 41 controls the communication interface 39 to send the undertaking conditions read in step S801 to the first information processing apparatus 12. After the undertaking conditions are sent, the process proceeds to step S805.

In step S805, the controller 41 determines whether unmatched recruiting conditions in the memory 40 have been all checked with regard to whether to match any undertaking conditions. In the case in which not all the unmatched recruiting conditions have been checked, the process returns to step S800. In the case in which all the unmatched recruiting conditions have been checked, the matching processing is ended.

Next, appointment notification processing performed by the controller 41 of the second information processing apparatus 14 in the present embodiment is described with reference to a flowchart in FIG. 15. The appointment notification processing is started when, for example, a decision on appointment indicating that a physician is appointed is received from the first information processing apparatus 12.

In step S900, the controller 41 stores, in the memory 40, an indication that a match has been confirmed between the undertaking conditions and the recruiting conditions received together with the decision on appointment. After the indication is stored, the process proceeds to step S901.

In step S901, the controller 41 generates a notification of appointment notification including a name of the medical facility 16, an arrival time at which the vehicle 10 is expected to arrive at a pickup location, and authentication information that are received together with the decision on appointment. After the notification of appointment is generated, the process proceeds to step S902.

In step S902, the controller 41 controls the communication interface 39 to send the notification of appointment generated in step S901 to the first terminal apparatus 13 sending the undertaking conditions received together with the decision on appointment. After the notification of appointment is sent, the appointment notification processing is ended.

The second terminal apparatus (the on-board apparatus) 15 according to the present embodiment configured as described above includes the input interface 25 configured to detect a user input for designating a relative position, the communication interface 22 configured to receive, from the first information processing apparatus 12, the first sound detected at the relative position and/or the first subject image detected at the relative position, and the output interface 24 configured to output the first sound and/or the first subject image. With this configuration, the second terminal apparatus 15 enables a physician travelling by using the vehicle 10 equipped with the second terminal apparatus 15 to provide a remote medical service, and thus, it is possible to efficiently use the physician's travel time. Particularly, the vehicle 10 can notify, by indicating a relative position, a patient via the first information processing apparatus 12 that which particular part the physician in the vehicle 10 desires to view or hear by auscultation, such that the vehicle 10 enables the physician in the vehicle 10 to recognize images and sound at the particular part of the patient in the medical facility 16 equipped with the first information processing apparatus 12, or the like. As such, while efficiently using the physician's travel time, the vehicle 10 can achieve more accurate medical services in comparison to the case of using just a videophone. And as a result, the vehicle 10 can reduce load on physicians for work other than examination and treatment.

Furthermore, the second terminal apparatus 15 of the present embodiment sends to the vehicle 10 control information for controlling the vehicle 10 to reach a stopover point by a designated time and then to travel to a destination. With this configuration, the second terminal apparatus 15 allows a physician to start examination immediately after a time designated by the physician who is picked up by the vehicle at a stopover point.

Further, the second terminal apparatus 15 of the present embodiment includes information for controlling the vehicle to travel via a plurality of stopover points and reach a last stopover point of the plurality of stopover points by a designated time in control information. With this configuration, the second terminal apparatus 15 allows every physician who is picked up by the vehicle at any of the stopover points to start examination at a corresponding designated time.

Moreover, in the second terminal apparatus 15 of the present embodiment, the designated time is a time that precedes, by a buffer time, a scheduled medical service start time of the medical facility 16 and the stopover point is a pickup location at which a physician determined by the medical facility 16 picked up by the vehicle 10. With this configuration, the second terminal apparatus 15 enables the vehicle 10 to reach a pickup location of a physician determined by the medical facility 16 by a scheduled medical service start time. As a result, the second terminal apparatus 15 enables the physician to get in the vehicle by the scheduled medical service start time, and thus, the physician can start examination at the scheduled medical service start time.

Furthermore, in the second terminal apparatus 15 of the present embodiment, the final destination is a location of the medical facility 16. With this configuration, while the second terminal apparatus 15 can have the physician only perform examination until the vehicle reaches the medical facility 16, the physician can travel to the medical facility 16 to provide a treatment service such as administering an injection in which the physician needs direct contact with a patient.

Further, in the second terminal apparatus 15 of the present embodiment, the final destination is a location of a designated parking space. With this configuration, the second terminal apparatus 15 enables the vehicle 10 to function as a medical service facility especially for examination close to physician's homes.

Moreover, when the first information processing apparatus 12 of the present embodiment receives, in response to sending recruiting conditions to the second information processing apparatus 14, undertaking conditions matching the recruiting conditions from the second information processing apparatus 14, the first information processing apparatus 12 sends a decision on appointment with respect to undertaking conditions to the second information processing apparatus 14. With this configuration, the first information processing apparatus 12 can determine, by recruiting, a physician to provide a remote medical service by using the vehicle 10. Consequently, the first information processing apparatus 12 can easily request not only physicians belonging to the medical facility 16 but also physicians not belonging to the medical facility 16 to provide temporary examinations.

Furthermore, the first information processing apparatus 12 of the present embodiment designates a pickup location included in undertaking conditions as a stopover point. With this configuration, the first information processing apparatus 12 allows for readily setting stopover points on the vehicle 10.

While the present disclosure has been described with reference to the accompanying drawings and the examples, it should be understood that various changes and modifications based on the present disclosure may be easily made by those skilled in the art. These changes and modifications are therefore embraced in the scope of the present disclosure. For example, the functions and the like included in the constituents and steps may be rearranged in a logically consistent manner; a plurality of constituents or steps may be combined together or divided.

For example, part of the processing operation performed by the second terminal apparatus 15, the first information processing apparatus 12, the first terminal apparatus 13, or the second information processing apparatus 14 in the embodiment described above may be carried out by another apparatus.

Furthermore, for example, a general electronic device such as a smartphone or a computer may be configured to function as the first information processing apparatus 12 or the second information processing apparatus 14 according to the embodiment described above. Specifically, a program in which details of processing for implementing the function of, for example, the first information processing apparatus 12 according to the embodiment are written is stored in a memory of an electronic device; a processor of the electronic device reads and runs the program. Thus, the disclosure according to the present embodiment may be implemented as a program that can be run by a processor. The program may be downloaded via the network 17; or the program may be stored in a portable non-transitory recording/storage medium readable by electronic devices and the program may be read from the medium by an electronic device.

Additionally, for example, while in the embodiment described above the first information processing apparatus 12 is configured to output, by using the output interface 30, a relative position received from the second terminal apparatus 15, the configuration may include an actuator configured to move the contact-type sound collection sensor and the wide-angle camera or the front end of the electronic endoscope, which are included in the sensor 29, to the relative position. With this configuration, the actuator enables the sensor 29 to detect the first sound and the first subject image at the relative position on a living body.

The invention claimed is:

1. A first information processing apparatus to be installed in a medical facility, the first information processing apparatus comprising:
    a sensor;
    a communication interface configured to:
        send recruiting conditions including a clinical department and a medical service request time, to a second information processing apparatus, the clinical department being related to a remote medical examination requested to be performed at the medical service request time; and
        in response to the sent recruiting conditions, receive undertaking conditions including a clinical department, a medical service available time, and a pickup location that are related to a physician who does not belong to the medical facility, from the second information processing apparatus, the clinical department of the received undertaking conditions being identical to the clinical department of the sent recruiting conditions and the medical service available time involving the medical service request time; and
    a controller configured to:
        decide whether to appoint the physician depending on whether the pickup location included in the received undertaking conditions is apart from a location of the medical facility by a distance equal to or greater than a threshold; and
        upon deciding to appoint the physician, determine the pickup location included in the undertaking conditions to be a stopover point, wherein
    the communication interface is configured to:

notify the second information processing apparatus of whether the physician is decided to be appointed by the controller;

send a designated time, the stopover point, and a destination, to an on-board apparatus provided in a vehicle, thereby causing the on-board apparatus to control the vehicle to reach the stopover point by the designated time and pick up the physician, and then to travel to the destination; and after the vehicle reaches the stopover point and picks up the physician, receive position information indicating a position on a living body targeted for the remote medical examination, from the on-board apparatus, the position being designated by the physician on board the vehicle, the sensor is configured to detect, at the position indicated by the position information received by the communication interface, a sound of the living body and/or a subject image of the living body, and the communication interface is configured to send the sound and/or the subject image detected by the sensor, to the on-board apparatus.

2. An information processing system comprising:
the first information processing apparatus according to claim 1; and
the on-board apparatus, wherein
the on-board apparatus is configured to:
  detect a user input for designating the position;
  send the position information to the first information processing apparatus;
  receive, from the first information processing apparatus, the sound and/or the subject image; and
  output the sound and/or the subject image.

3. An information processing system comprising:
the first information processing apparatus according to claim 1; and
the second information processing apparatus, wherein
the second information processing apparatus is configured to:
  upon receiving the recruiting conditions from the first information processing apparatus, retrieve the undertaking conditions out of one or more undertaking condition sets stored in a memory; and
  send the undertaking conditions to the first information processing apparatus.

4. The information processing system according to claim 3, further comprising one or more terminal apparatuses configured to communicate with the second information processing apparatus, wherein
the second information processing apparatus is configured to:
  receive the one or more undertaking condition sets from the one or more terminal apparatuses; and
  store the one or more undertaking condition sets in the memory.

5. The information processing system according to claim 4, wherein
the second information processing apparatus is configured to, upon being notified that the physician is decided to be appointed, inhibit the undertaking conditions from being retrieved and sent in response to recruiting conditions from this point forward.

6. The first information processing apparatus according to claim 1, wherein
the designated time is a time that precedes, by a buffer time, a scheduled medical service start time of the medical facility.

7. The first information processing apparatus according to claim 1, wherein
the destination is the location of the medical facility.

8. The first information processing apparatus according to claim 1, wherein
the communication interface is configured to send authentication information to the on-board apparatus, thereby causing the on-board apparatus to authenticate the physician at the stopover point using the authentication information.

9. The first information processing apparatus according to claim 1, further comprising a display configured to output a schematic drawing of a human body, the schematic drawing including a sign that indicates the position indicated by the position information received by the communication interface, wherein
the sensor is configured to detect, at the position indicated by the sign included in the schematic drawing output by the display, the sound of the living body and/or the subject image of the living body.

10. An information processing method implemented by a first information processing apparatus installed in a medical facility, the information processing method comprising:
sending recruiting conditions including a clinical department and a medical service request time, to a second information processing apparatus, the clinical department being related to a remote medical examination requested to be performed at the medical service request time;
in response to the sent recruiting conditions, receiving undertaking conditions including a clinical department, a medical service available time, and a pickup location that are related to a physician who does not belong to the medical facility, from the second information processing apparatus, the clinical department of the received undertaking conditions being identical to the clinical department of the sent recruiting conditions and the medical service available time involving the medical service request time;
deciding whether to appoint the physician depending on whether the pickup location included in the received undertaking conditions is apart from a location of the medical facility by a distance equal to or greater than a threshold;
upon deciding to appoint the physician, determining the pickup location included in the undertaking conditions to be a stopover point;
notifying the second information processing apparatus of whether the physician is decided to be appointed;
sending a designated time, the stopover point, and a destination, to an on-board apparatus provided in a vehicle, thereby causing the on-board apparatus to control the vehicle to reach the stopover point by the designated time and pick up the physician, and then to travel to the destination;
after the vehicle reaches the stopover point and picks up the physician, receiving position information indicating a position on a living body targeted for the remote medical examination, from the on-board apparatus, the position being designated by the physician on board the vehicle;
detecting, at the position indicated by the received position information, a sound of the living body and/or a subject image of the living body; and sending the detected sound and/or the detected subject image, to the on-board apparatus.

\* \* \* \* \*